(12) United States Patent
Rudan et al.

(10) Patent No.: US 8,177,850 B2
(45) Date of Patent: May 15, 2012

(54) JOINT PLACEMENT METHODS AND APPARATUSES

(75) Inventors: John Rudan, Kingston (CA); Randy E. Ellis, Kingston (CA); Manuela Kunz, Kingston (CA)

(73) Assignee: iGO Technologies, Inc., Inverary (CA)

( * ) Notice: Subject to any disclaimer, the term of this patent is extended or adjusted under 35 U.S.C. 154(b) by 361 days.

(21) Appl. No.: 12/339,791

(22) Filed: Dec. 19, 2008

(65) Prior Publication Data

US 2009/0164024 A1 Jun. 25, 2009

Related U.S. Application Data

(63) Continuation of application No. PCT/CA2007/001082, filed on Jun. 19, 2007.

(60) Provisional application No. 60/814,547, filed on Jun. 19, 2006.

(51) Int. Cl.
*A61F 2/32* (2006.01)
(52) U.S. Cl. ............. 623/22.15; 623/22.21; 623/22.11
(58) Field of Classification Search ........... 623/20.22, 623/20.36, 22.15
See application file for complete search history.

(56) References Cited

U.S. PATENT DOCUMENTS

| 6,205,411 | B1 * | 3/2001 | DiGioia et al. ............ 703/11 |
| 6,711,431 | B2 | 3/2004 | Sarin et al. |
| 7,001,346 | B2 | 2/2006 | White |
| 2003/0176783 | A1 | 9/2003 | Hu |
| 2004/0181149 | A1 | 9/2004 | Langlotz et al. |
| 2006/0095047 | A1 | 5/2006 | de la Barrera |

OTHER PUBLICATIONS

Canadian Intellectual Property Office, Office Action, May 19, 2011.

* cited by examiner

*Primary Examiner* — Thomas J Sweet
*Assistant Examiner* — Brian Dukert
(74) *Attorney, Agent, or Firm* — Krugliak, Wilkins, Griffiths & Dougherty Co., L.P.A.; David P. Dureska; Brent L. Moore

(57) ABSTRACT

Systems and methods for determining placement of prosthetic components in joint including defining patient-specific frame of reference for joint, determining patient-specific postoperative range of motion of joint, evaluating patient-specific range of motion of joint, automatically planning placement of components balancing need for range of motion with prosthesis stability through bony coverage, and applying manual adjustments to the automatically planned placement of component by giving greater or lesser weight to need for range of motion or prosthesis stability through bony coverage. Apparatuses for defining center of prosthetic femoral head and axis of prosthetic femoral neck including primary cylinder, first alignment receptacle and second alignment receptacle, and a divot on exterior of primary cylinder, divot having normal parallel to longitudinal axis of second alignment receptacle and position of the divot being translated toward an opening of the first alignment receptacle on the primary cylinder. Methods for using apparatuses. Apparatus for mounting spatially tracked device to impactor for impacting prosthetic cup into reamed socket.

6 Claims, 24 Drawing Sheets

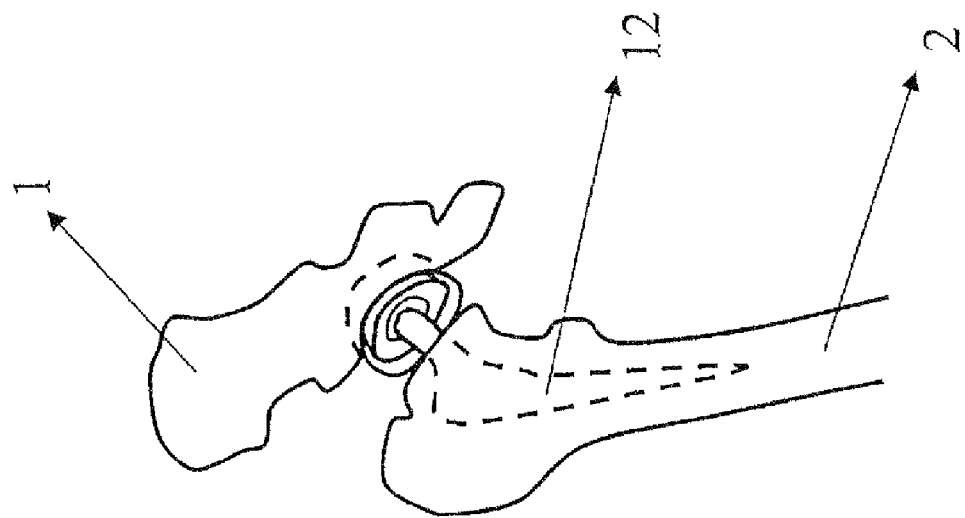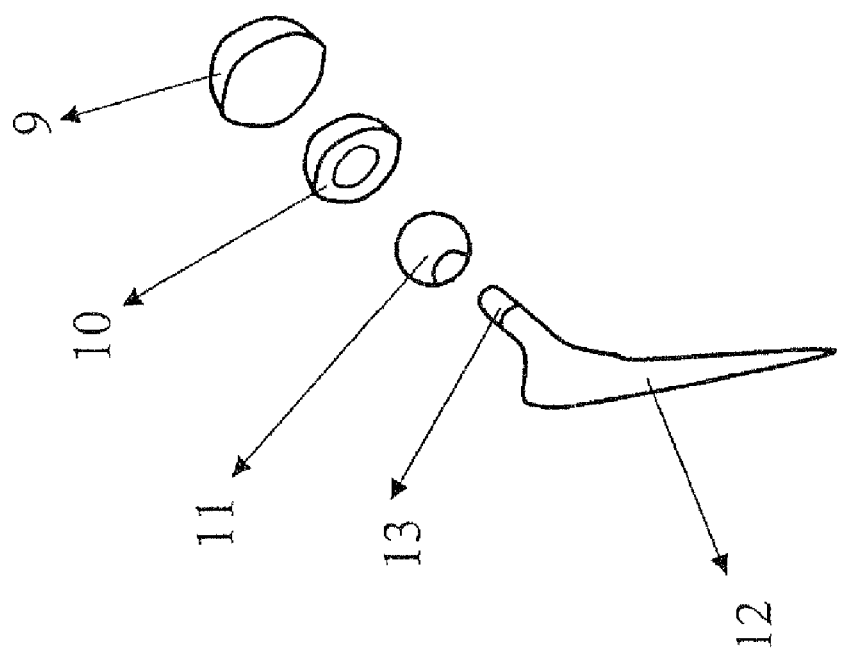
FIG. 2

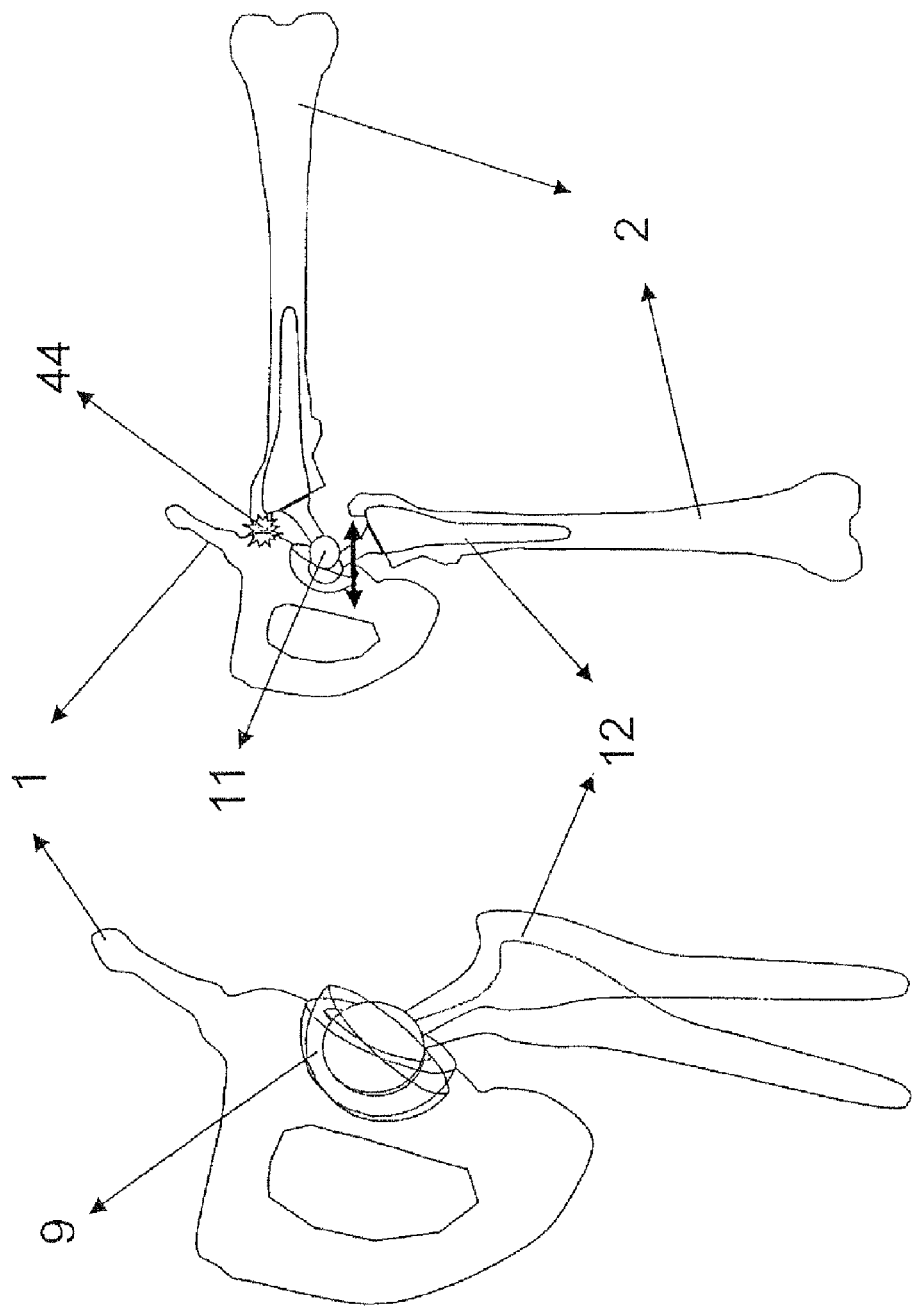

JOINT PLACEMENT METHODS AND APPARATUSES

CROSS-REFERENCE TO RELATED APPLICATIONS

This application is a continuation of, and claims the benefit of, International Patent Application No. PCT/CA2007/001082, filed on Jun. 19, 2007, which claims the benefit of U.S. Provisional Patent Application Ser. No. 60/814,547, filed on Jun. 19, 2006. The entire disclosure of U.S. Provisional Patent Application Ser. No. 60/814,547 is hereby incorporated by reference.

TECHNICAL FIELD

The invention relates to joint placement generally, more specifically to placement of prosthetics for joint repair.

BACKGROUND ART

Joint repair, or arthroplasty, is a surgical intervention for repairing defects or injuries of a joint. The goal is to restore as much normal function as possible while at the same time reducing or eliminating pain and discomfort. Joint repairs allow patients to regain mobility, continue contributing to society and enjoy a greater quality of life.

Arthroplasty attempts to correct how two bones interact with one another. For example, in a hip the femoral head 6 fits into the acetabulum 3 of the pelvis 1 creating a ball and socket type joint. The movement of the femur 2 in the pelvis 1 is constrained by both the bony-to-bony interaction as well as the function of the soft tissue (ligaments and muscle) attached to both bony anatomies. Arthroplasty involves resurfacing or replacing the natural surfaces of the bones where they interact (the articular surface). For example, referring to FIG. 2, when performing hip arthroplasty a surgeon replaces or resurfaces the femoral head 6 and acetabulum 3 with artificial implants. To help restore function the soft tissue may also be modified, such as through a partial release of its attachment to bone.

Intervention to correct problems of a joint suffers from difficulty in finding an optimal implant placement including position and orientation. Problems arising from incorrect placement may involve, among other symptoms, post surgical pain, limited range of motion, dislocation, post surgical fracture, premature implant failure, and adverse biologic response consequent to any of the preceding problems.

The extent of the problem is evidenced in high revision rates. The majority of arthroplasties (86%) performed in U.S. are on the hip or knee (American Academy of Orthopaedic Surgeons, "Musculoskeletal Conditions in the United States", p. 121, 1999). According the American Academy of Orthopaedic Surgeons, 54,000 of the total hip and knee procedures done in the U.S. each year are revision surgeries (American Academy of Orthopaedic Surgeons Bulletin, "Number of arthroplasties to increase dramatically", Vol. 50, No. 1, 2002).

Dislocation following arthroplasty is a major factor in early failure with an incidence rate, for example, of 3-5% for hips (for discussion see McCullum, D E, W J Gray, "Dislocation After Total Hip Arthroplasty—Causes and Prevention", Clinical Orthopaedics and Related Research, December (261), pp. 159-170, 1990). The common reason for dislocation is the position and orientation of the artificial implants, particularly of the acetabulum implant in hip arthroplasty (for discussion see Lewinnek et al., "Dislocation after Total Hip-Replacement Arthroplasties", Journal Bone Joint Surgery, 60-A(2), pp. 217-220, 1978). When the implants are not correctly placed, impingements 4 between the implant components and/or anatomy can occur. These points of impingement cause a lever effect and potentially result in dislocation. Besides being painful and stressful for the patient, it also leads to abductor tissue damage, which has a detrimental long-term effect on the stability of the hip joint.

A number of methods and apparatuses for assisting in arthroplasties have been developed. These methods and apparatuses include mechanical jigs and computer-assistance (both image-based and imageless). A common aspect is the use of an anatomic reference such as the sagittal and coronal planes of the patient, or the pelvic plane as defined by the pubic tubercles 85, 86 and anterior superior iliac spines 7, 8.

Mechanical guides attempt to address the problem by providing surgical tools which, when placed in a specific manner provide a referencing system for determining implant placement (for discussion see Eggli et al., "The value of preoperative planning for total hip arthroplasty", Journal Bone Joint Surgery, 80-B(4), pp. 382-390, 1998). These solutions can suffer from one or more of the following problems.

They are based on standardized placement specifications that may not apply to an actual patient. The guides depend on precise, but difficult, placement within anatomy. The external frame of reference can change dramatically based on patient anatomy, positioning and surgical approach. They typically do not allow for soft tissue effects. The guides provide a static placement for a problem that is inherently kinematic in nature. The guides provide limited flexibility for anatomical variability.

Image-based computer assisted solutions also exist. These solutions typically use either CT (for discussion see DiGioia et al., "HipNav Technical Paper", Centre for Medical Robotics and Computer Assisted Surgery) or fluoroscopy (Tannast et al., "Accuracy and potential pitfalls of fluoroscopy-guided acetabular cup placement", Computer Aided Surgery, Vol. 10, Issue 5-6, pp. 329-336) to capture images of the anatomy. Used in conjunction with a spatial tracking device, the images are then used to anatomically plan the implant placement, in either a manual or semi-automatic manner. These systems then provide the surgeon with guidance to transfer the planned placement onto the patient anatomy.

3D solutions (typically based on Computer-Tomography or Magnetic Resonance Imaging) can have one or more of the following limitations. They require pre-surgical scanning of the patient consuming more time, increasing cost and exposing the patient to additional radiation. Planning based on scans and reconstruction of the bony anatomy fail to account for the important and significant contribution of soft tissue to the function of the joint. Three-dimensional scans are typically used to create a surface model of the anatomy. This adds time and has potential error associated with it. Complex, time consuming and potentially error-prone registration of the patient to the scan must be performed intra-operatively. A pre-surgical planning step is often used with CT-based systems. Such planning is scheduled separately from the surgery and consumes more time and thus increases cost. Pre-operative imaging does not allow for intra-operative updating.

2D (typically fluoroscopy) solutions can have one or more of the following limitations. The prescribed images can be difficult to obtain (e.g., lateral image of the hip). There is additional radiation exposure to the patient and operating room staff. Fluoroscopy requires tracking of the c-arm (x-ray image intensifier) and image processing to account for image distortion and to characterize the c-arm geometry. The hardware necessary to do this increases cost. The additional setup can be complicated and time-consuming. The image processing requires use of software algorithms that must be written, maintained and presents another opportunity for introducing error. Picking 3D anatomical landmarks from 2D images, particularly on complex anatomy and/or lower quality images is difficult and error-prone.

Non-image, computer assisted solutions also exist (for discussion see Jansen et al., "Computer-Assisted Hip Replacement Surgery, patent US2004/0230199-A1). They make using of spatial tracking technology to detect the location of the patient and surgical instruments. These solutions attempt to solve the issues involved with image-based solutions by having the surgeon palpate specific anatomical points in order to define properties of the anatomy (e.g., the pelvic plane) and/or require 'painting' of the local bony anatomy in order to morph standardized anatomical models to the patient's anatomy. Palpation of anatomy to define anatomical properties (axes, planes, etc.) has difficulty in accurately palpating anatomical features, e.g., the right 85 and left pubic tubercles 86 and right 7 and left anterior superior iliac spine (ASIS) 8 for determining the pelvic plane. It can also have an increased risk of infection from percutaneous palpations outside the immediate joint replacement site. Extensive 'painting' of the local anatomy with a spatially tracked probe has one or more of the following shortcomings as well. Inaccessible anatomy for 'painting' (particularly with minimally invasive approaches). Painting is time consuming, which increases the procedure time. There is difficulty in maintaining probe-to-anatomy contact.

Current image-based and non-imaging computer assisted solutions attempt to define anatomical properties (axes, planes, etc.) for the purposes of guiding the user, and face one or more of the following problems. Solutions using anatomical properties prescribe implant placement based on standardized values derived from a large population. Standardized orientations are derived by using a sample population to determine what orientations result in the fewest complications and failures. These are defined relative to a standardized frame of reference, further removing the solution from the patient specific joint function. Not being patient specific they are not necessarily ideal, or even correct, for an individual. Whether point picking in images or palpating anatomy, the process for providing the inputs to calculate the anatomical properties is often difficult and error-prone. The anatomical properties are based on bony anatomy and fail to account for the critical contribution of soft tissue to the behaviour of joints.

Alternative methods and apparatuses for assisting in implant placement are desirable to assist in addressing one or more of the issues with existing methods and apparatuses.

DISCLOSURE OF THE INVENTION

In a first aspect the invention provides a method for determining placement of prosthetic components in a joint. The method includes defining a patient-specific frame of reference for the joint, determining patient-specific postoperative range of motion of the joint, evaluating patient-specific range of motion of the joint, automatically planning placement of the components balancing the need for range of motion with prosthesis stability through bony coverage; and applying manual adjustments to the automatically planned placement of the component by giving greater or lesser weight to the need for range of motion or prosthesis stability through bony coverage.

The method may include defining a patient specific frame of reference by recording passive joint movements and evaluation of the directions of the movements.

The method may include defining a patient specific frame of reference from passive movements by recording movements that are only limited by soft tissue characteristics, bony to bony impingement, bony to prosthesis impingement, soft tissue to bony impingement, soft tissue to soft tissue impingement, and/or soft tissue to prosthesis impingement.

The method may include evaluating the patient-specific range of motion by detecting impingement. The method may include evaluating the patient-specific range of motion by calculating and comparing range of motion boundaries based on patient specific lifestyle requirements and detection of undesirable laxity or tightness in the soft tissue.

The method may include determining postoperative outcome of the joint repair by considering component stability and postoperative kinematic behaviour. The method may include automatically planning placement of the components considering the component stability and postoperative kinematics.

Automatically planning placement of the components may consider component stability and postoperative kinematics to simulate and evaluate the results of a multitude of component placements.

In a second aspect the invention provides a method of determining desired placement of a cup within an anatomical joint having a socket and having a stem with a center of rotation. The cup has a given range of motion for the stem. The method includes placing the cup in the socket such that movement of a center of rotation of the cup is limited, while rotation of the cup about the center of rotation is permitted, reducing the stem and cup such that the center of rotation of the stem and the center of rotation of the cup are concentric, determining a range of motion of the joint by moving the stem, and aligning the range of motion of the cup and the determined range of motion of the joint.

The method may include palpating a rim of the socket in order to determine a plane of the rim, and, at the same time as aligning the range of motion of the cup and the determined range of motion of the joint, aligning the cup within the socket to provide desired bony coverage to the cup within the rim.

The method may include modifying the range of motion of the joint to improve the alignment of the range of motion of the cup and the range of motion of the socket. The method may include repeating steps of the method after modification.

The method may include modifying the joint to change spatial placement of the cup within the socket to improve bony coverage to the cup within the rim. The method may include repeating steps of the method after modification.

In a third aspect the invention provides an apparatus for defining the center of a prosthetic femoral head and axis of a prosthetic femoral neck. The apparatus includes a primary cylinder where a first end of the cylinder is adapted for placement over an exposed neck of a prosthetic femoral stem such that a longitudinal axis of the primary cylinder is congruent with an axis of the prosthetic femoral neck. The apparatus further includes a first alignment receptacle at an opposing second end of the cylinder, the first alignment receptacle having a longitudinal axis congruent with the longitudinal axis of the primary cylinder and the receptacle adapted to stop a spatially tracked probe at a known location relative to the centre of the prosthetic femoral head. The apparatus further includes a second alignment receptacle fixed relative to the primary cylinder, the receptacle having a longitudinal axis normal to the longitudinal axis of the primary cylinder, adapted to receive a spatially tracked probe aligned with the longitudinal axis of the alignment receptacle. The apparatus further includes a divot on the exterior of the primary cylinder. The divot has a normal parallel to the longitudinal axis of the second alignment receptacle and the position of the divot being translated toward an opening of the first alignment receptacle on the primary cylinder.

In a fourth aspect the invention provides a method for using the apparatus for defining the center of a prosthetic femoral head and axis of a prosthetic femoral neck to determine the center of the prosthetic femoral head and the axis of the prosthetic femoral neck. The method includes placing the first end of the primary cylinder over an exposed neck of a prosthetic femoral stem. The method further includes performing one of the following steps, i) placing a spatially tracked probe in the first alignment receptacle, ii) placing the spatially tracked probe in the second alignment receptacle and rotating the apparatus about the axis of the prosthetic femoral neck; and iii) placing the spatially tracked probe in the second alignment receptacle and placing the probe in the divot.

In a fifth aspect the invention provides an apparatus for mounting a spatially tracked device to an impactor for impacting a prosthetic cup into a reamed socket. The apparatus includes a tubular cylinder adapted to be mounted about a shaft of the impactor such that a longitudinal axis of the cylinder is aligned with a longitudinal axis of the impactor and is able to rotate about the shaft and move freely along the shaft. The apparatus further includes a mount on the cylinder adapted to retain the spatially tracked device in a known orientation relative to the cylinder.

In a sixth aspect the invention provides a system for assisting in the placement of prosthetic components in a joint. The system includes a module for calculation of joint movements, a module for calculation of a functional reference system, a module for recording patient specific joint range of motion, and a module for evaluation of patient specific range of motion for impingement.

The system may include a module for automatically planning a placement for the prosthetic cup. The system may include a module for determining bony coverage boundaries such as the plane of the socket's rim.

The system may include a module for registration of a prosthetic femoral stem's femoral head center and neck axis. The system may include a module for navigating an impactor to place a prosthetic cup in a planned orientation. The system may include navigator technology, at least one output device, at least one central processing unit, wherein the modules are associated with the at least one central processing unit to receive inputs from the navigator technology and generate outputs for the at least one output device.

Other aspects of the invention will be evident from the detailed description and FIGS. provided herein.

BRIEF DESCRIPTION OF THE DRAWINGS

For a better understanding of the present invention and to show more clearly how it may be carried into effect, reference will now be made, by way of example, to the accompanying drawings which show the preferred embodiment of the present invention and in which:

FIG. 2 is a representation of a total hip arthroplasty.

FIGS. 11a and 11b show example factors in performing impingement checking for range of motion for the method of FIG. 2.

MODES FOR CARRYING OUT THE INVENTION

Figures 1A, 1B:
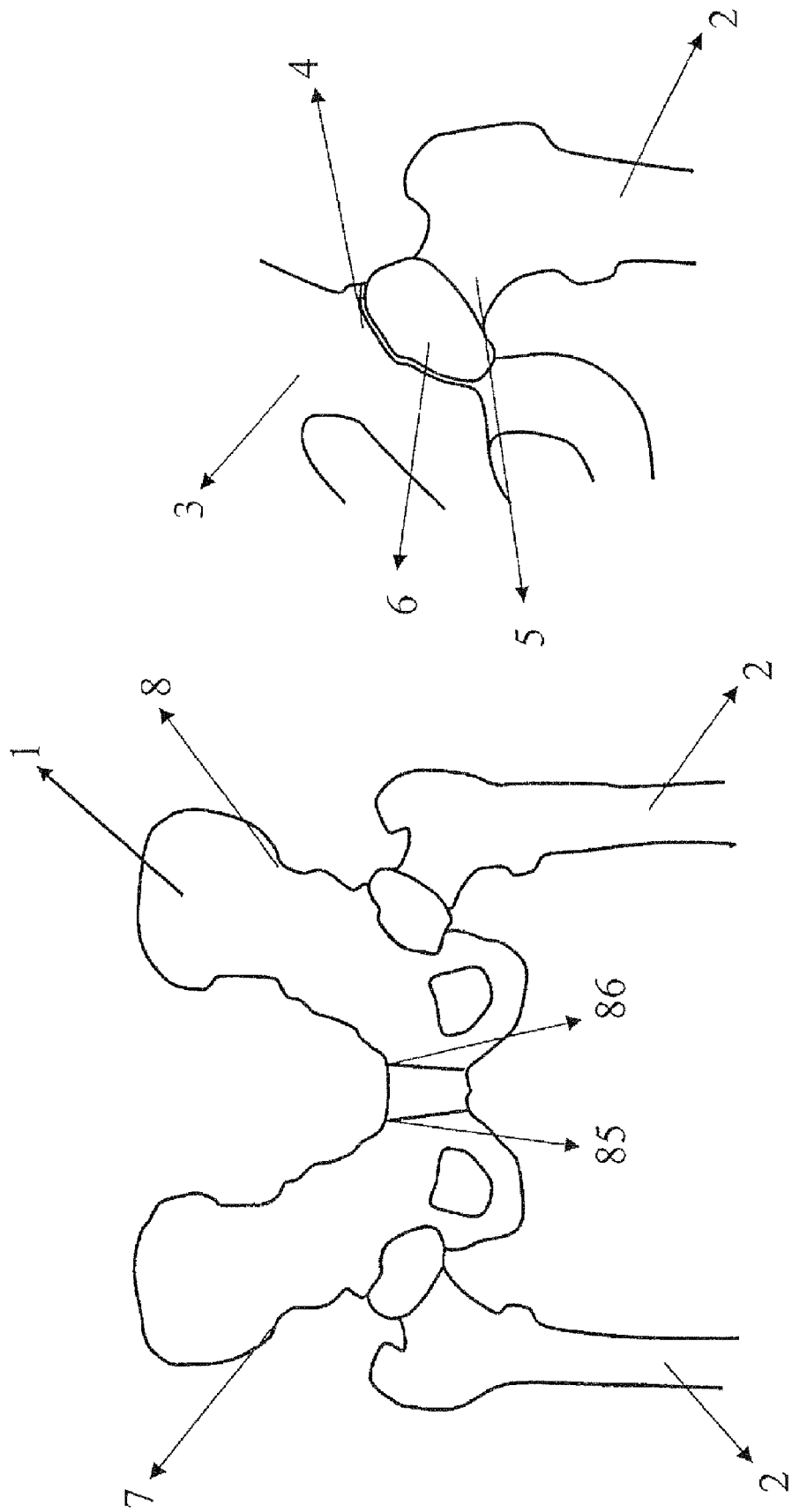
FIGS. 1a and 1b are skeletal representations of a human hip joint.
Figure 3:
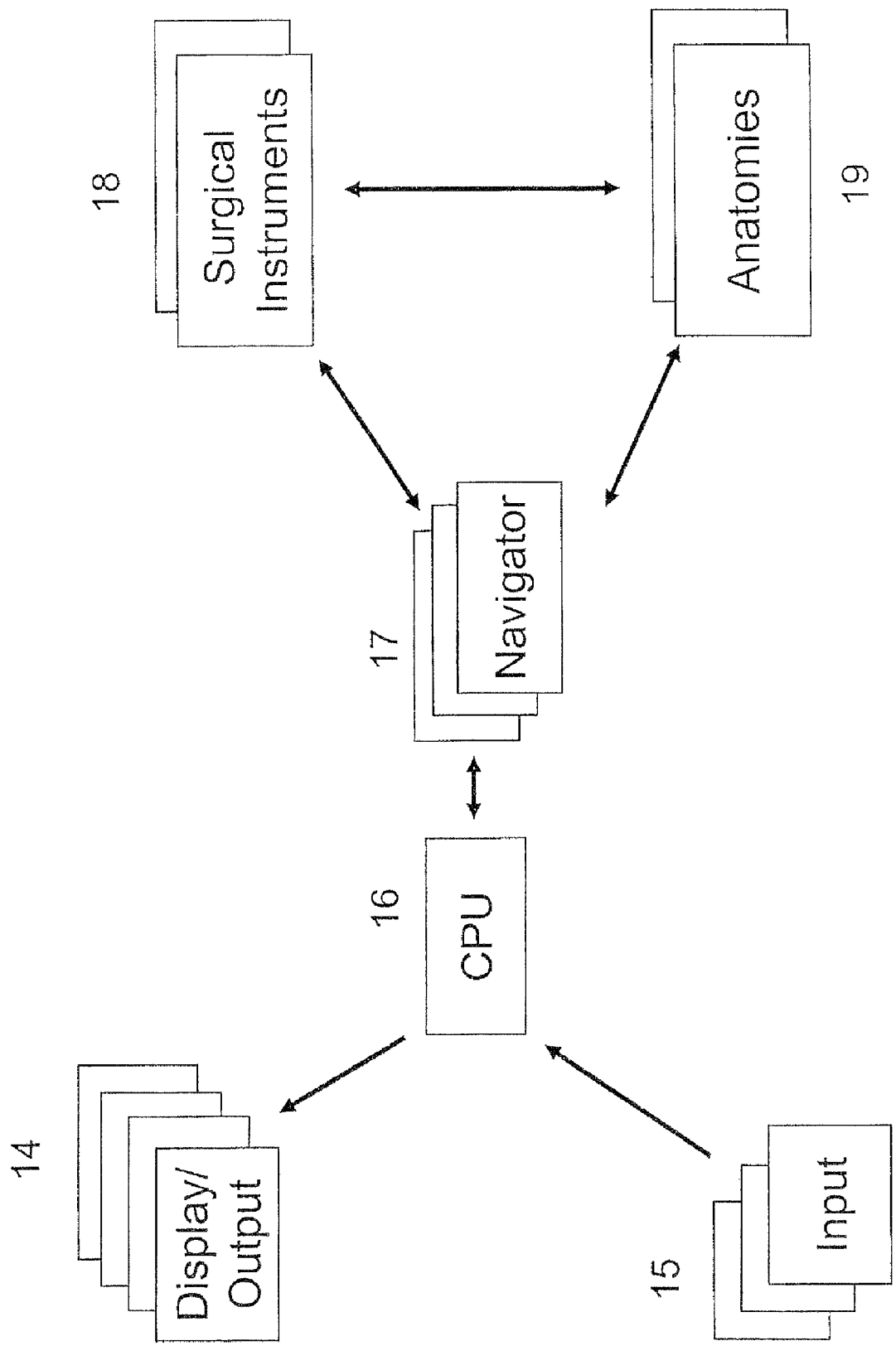
FIG. 3 is a block diagram illustrating example components of an embodiment of a system in accordance with an embodiment of an aspect of the invention.

Referring to FIG. 3, a system has a central processing unit(s) 16, one or more output devices 14, and navigator technology 17. The navigator technology 17 may be passive localization or active positioning technologies. The system also has input devices 15 for example, keyboard, mouse, foot pedal, button probes, or virtual keyboards, specialized surgical instruments 18, and devices for localizing anatomies 19 using navigator technology 17. The central processing unit(s) 16 has the computational power to process localization data, perform complex mathematical calculations and, optionally, perform image processing. The central processing unit(s) 16 also has associated modules to carry out the various features and functions described herein, examples of such modules will be described later herein. The modules may be software in memory accessible to the central processing unit(s) 16. There is a means for communication between the central processing unit(s) 16, the other apparatus components and, optionally, imaging systems and networking with other electronic systems such as, for example, imaging archives, inventory databases, and scheduling systems. The navigator technology 17 has the ability to determine the spatial pose (position and orientation) of objects in 3-dimensional space. The output device(s) 14 provides a means for a user of the system to receive feedback on planning and navigating placement of an artificial component. The output device(s) 14 are typically a display device, such as, for example, a computer monitor but may employ other forms of feedback such as, but not limited to, customized LCD, auditory or tactile devices.

Figure 24:
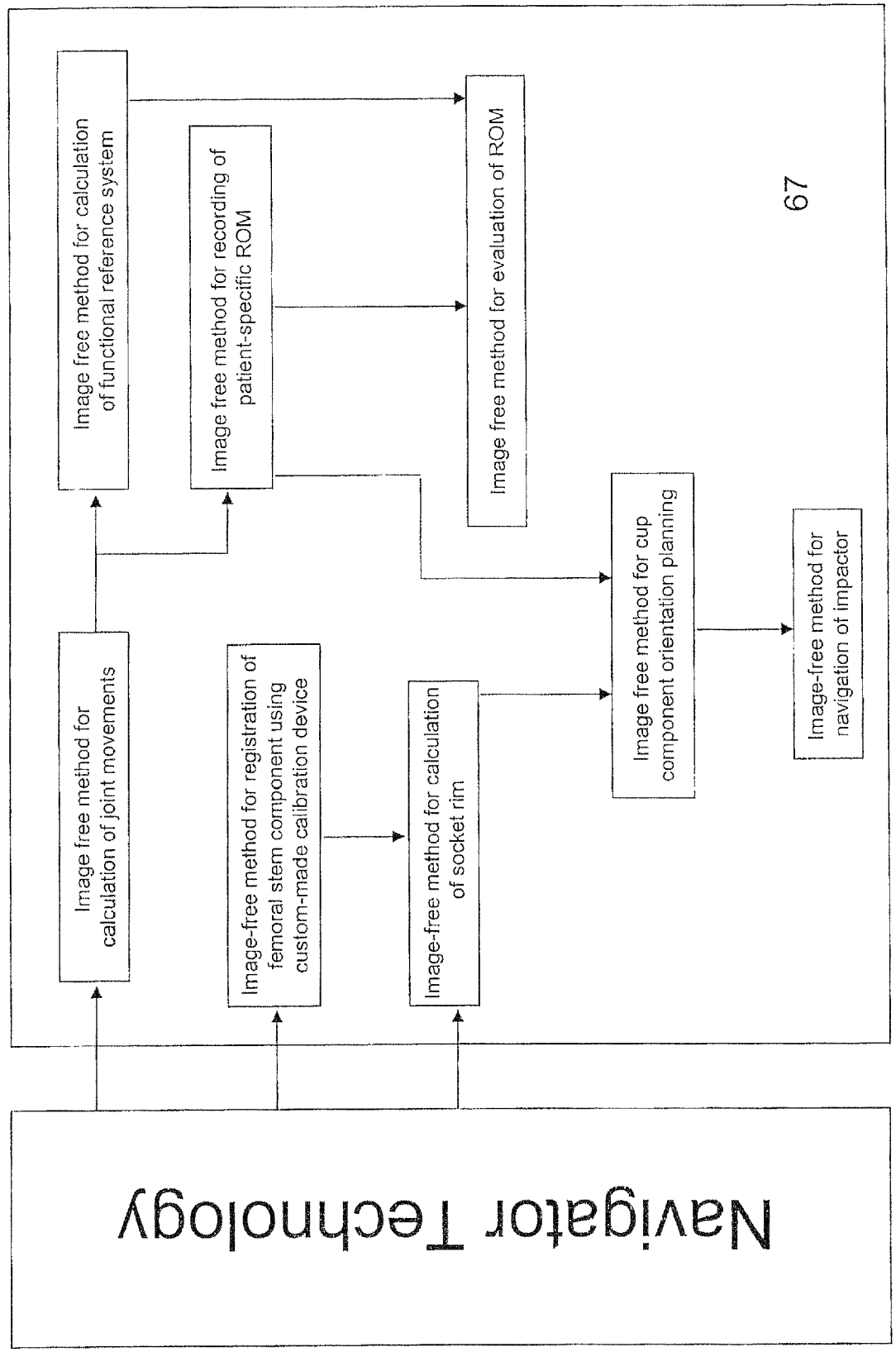
FIG. 24 illustrates modules of an embodiment of a system for use in total hip replacement.

For clarity and by way of example only, a method for determining placement of and an apparatus for an artificial component will be described in the context of a system having modules for performing a total hip replacement (FIG. 2) as embodied by the system modules constructed for this purpose shown in FIG. 24. It is to be recognized that the methods and apparatuses described herein can be applied to placement of other types of artificial components with consequent modifications, such as, for example, artificial components for knee replacements and shoulder replacements. Furthermore, and also for clarity and by way of example, the apparatus for employing the method will be limited to a single stand-alone computer for the central processing unit(s) 16, a computer monitor for the display device 37 and an optical spatial tracking system 35 for the navigator technology 17. Other components or combinations thereof could be used to provide the functions and features described herein, such as, for example, alternate spatial tracking technology based on electromagnetic, visible light, or acoustics technology.

Figure 4:
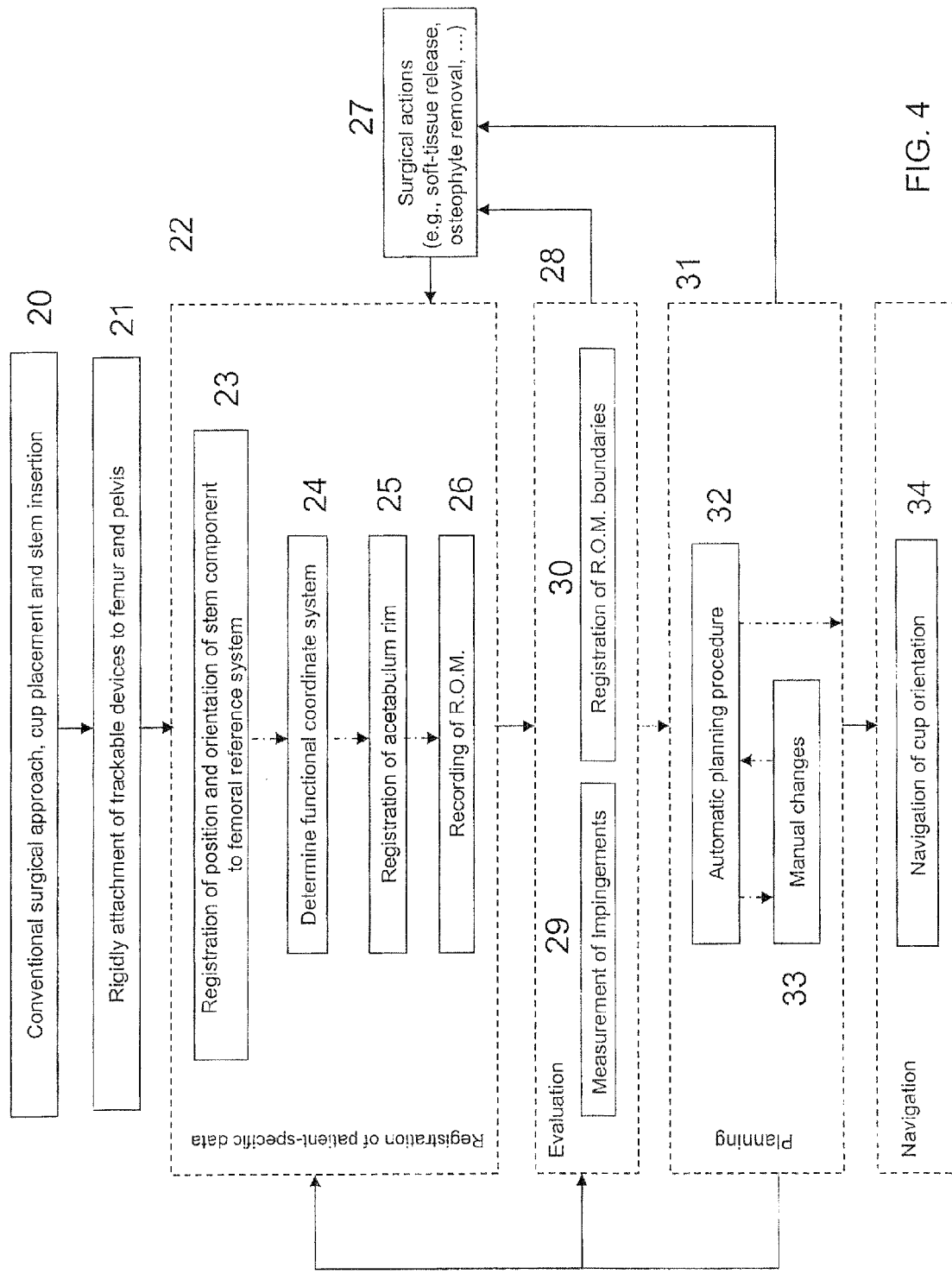
FIG. 4 is a flow chart illustrating a method in accordance with an embodiment as applied to a hip joint placement.

Referring to FIG. 4, a workflow for applying a method to a hip arthroplasty is shown.

Figure 5:
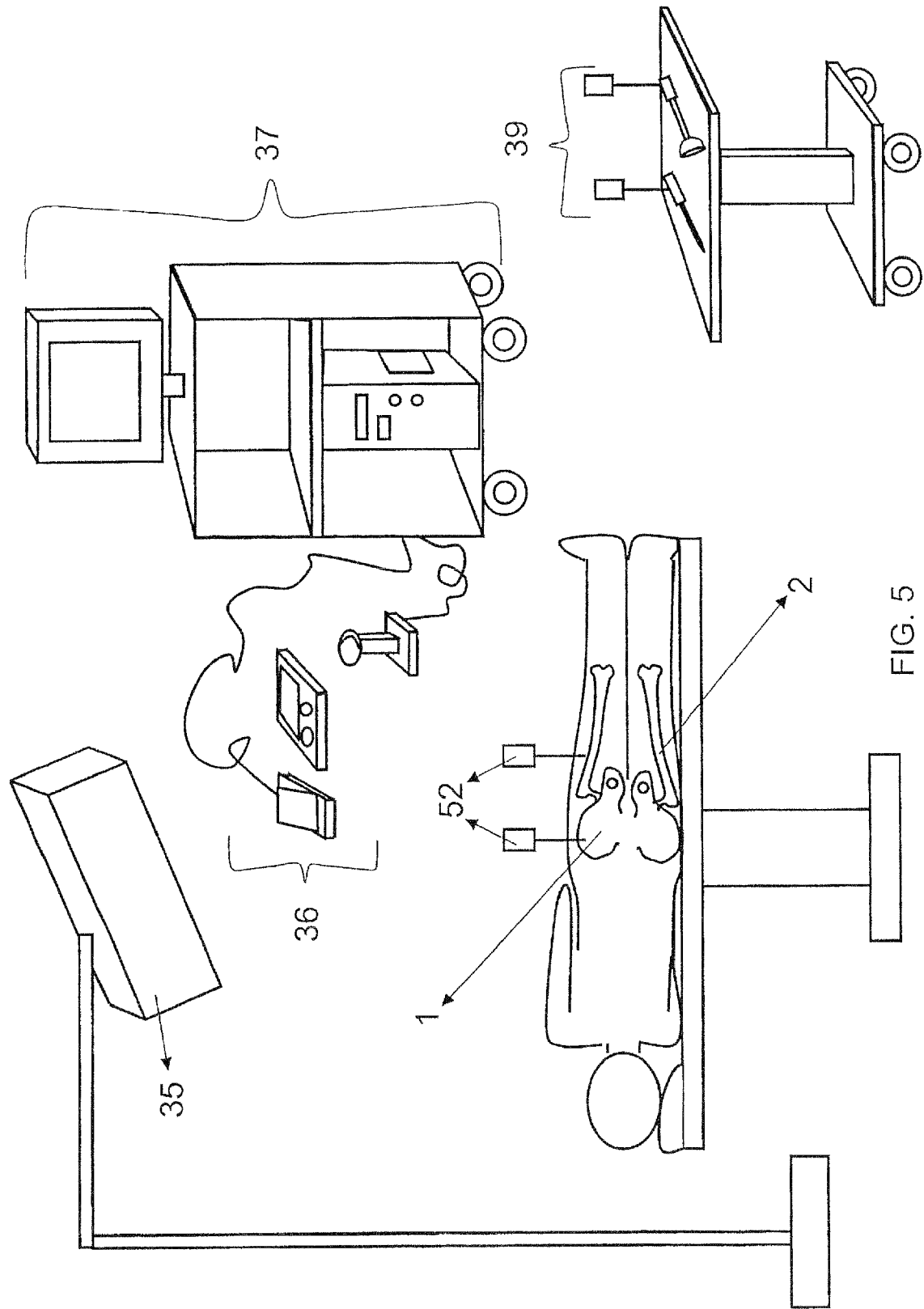
FIG. 5 is a schematic layout of the system of FIG. 3 as employed in a hip joint placement.
Figure 6:
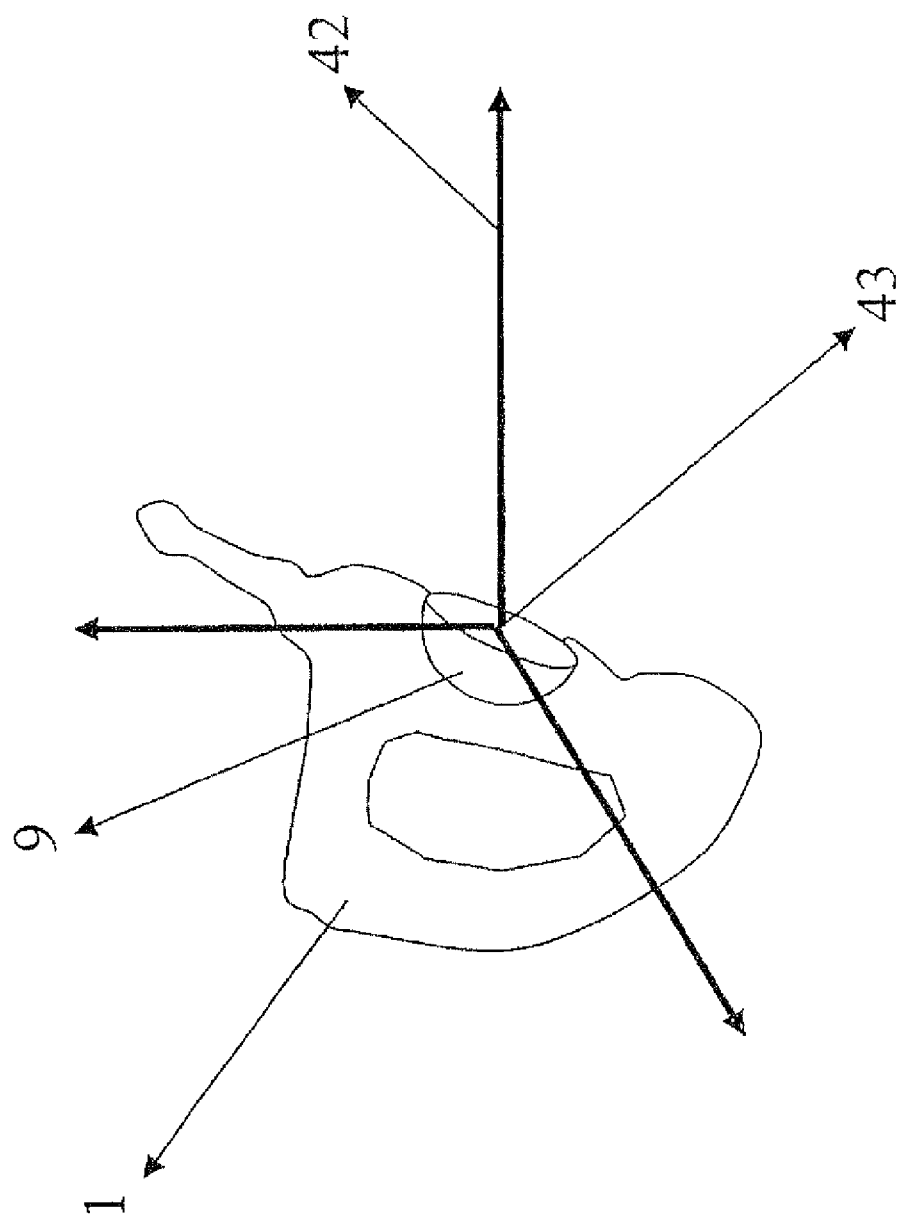
FIG. 6 illustrates an example functional coordinate system for use in the system of FIG. 3.
Figures 7A, 7B:
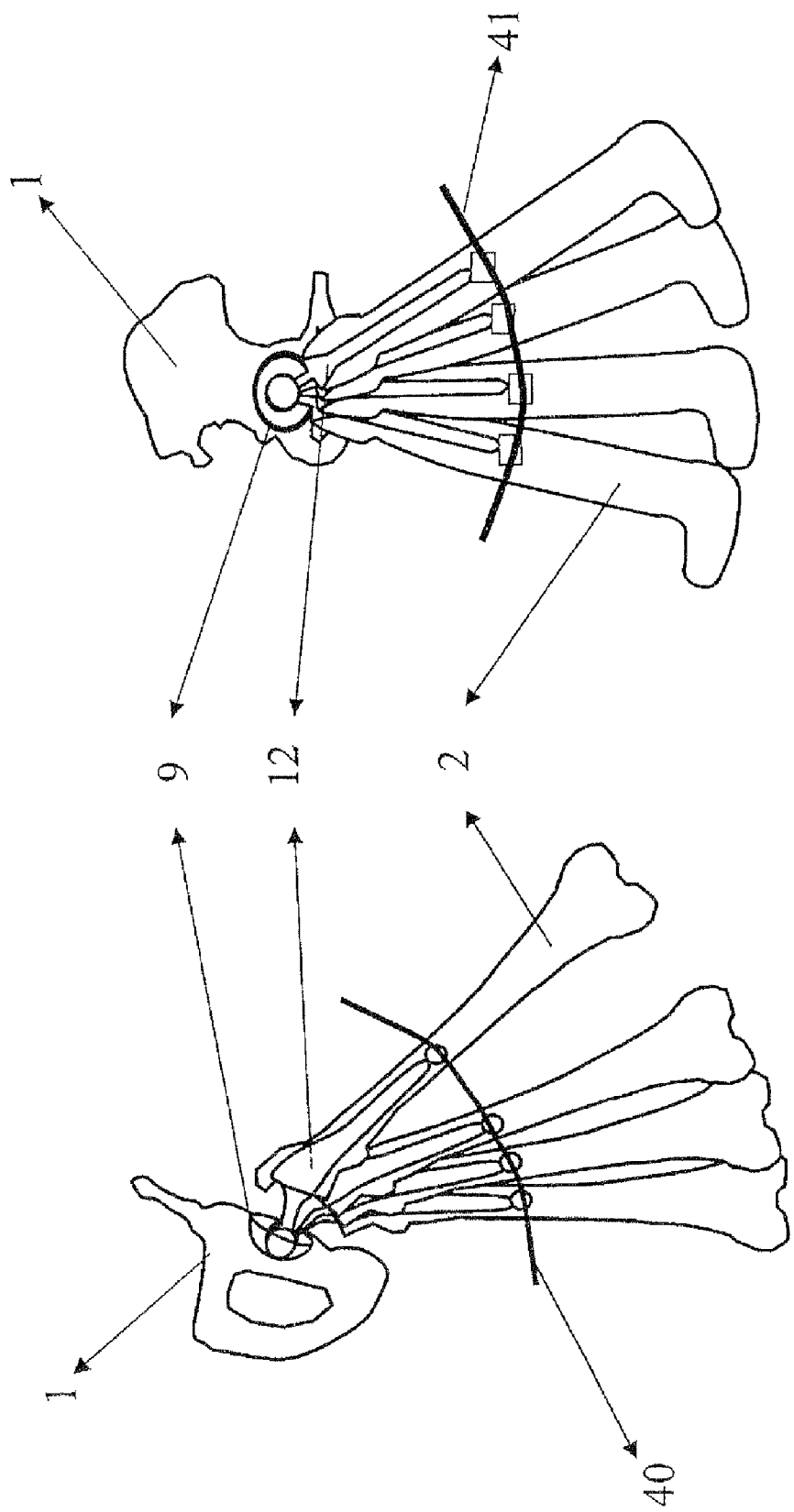
FIGS. 7a and 7b illustrate recording an example functional data for determination of functional coordinate system for the method of FIG. 6.
Figure 8B:
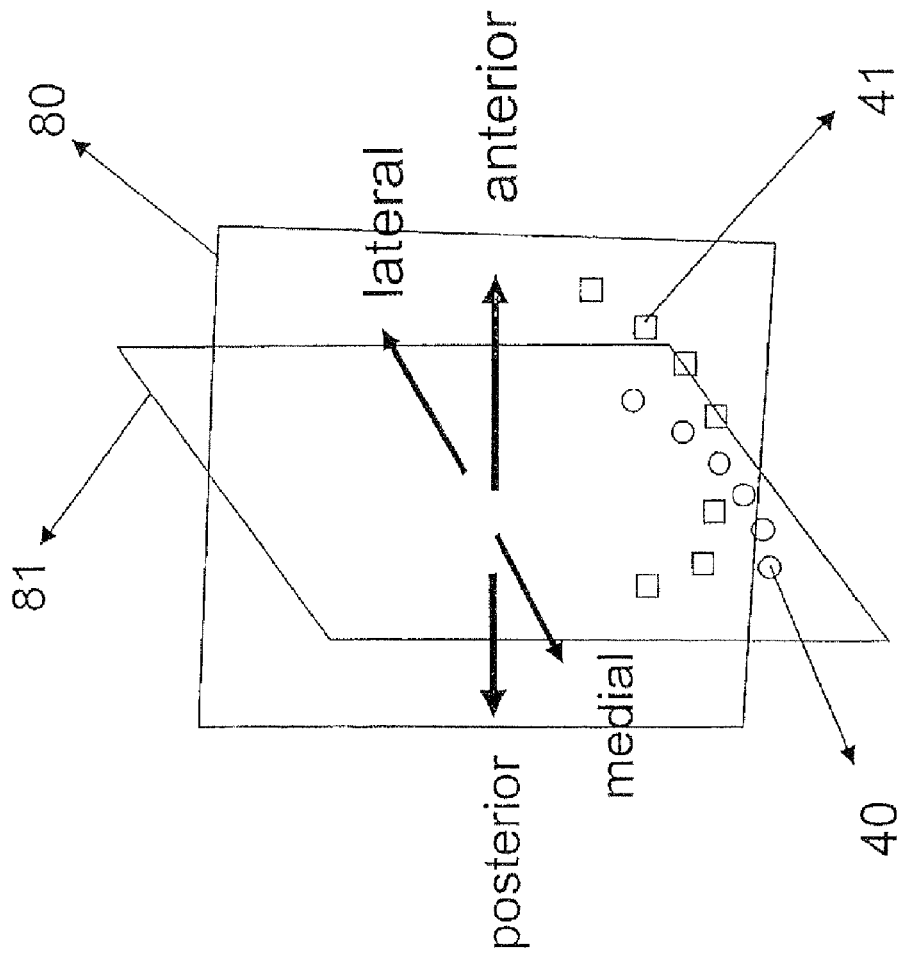
FIGS. 8a and 8b illustrate determining an example functional coordinate system.
Figure 8A:
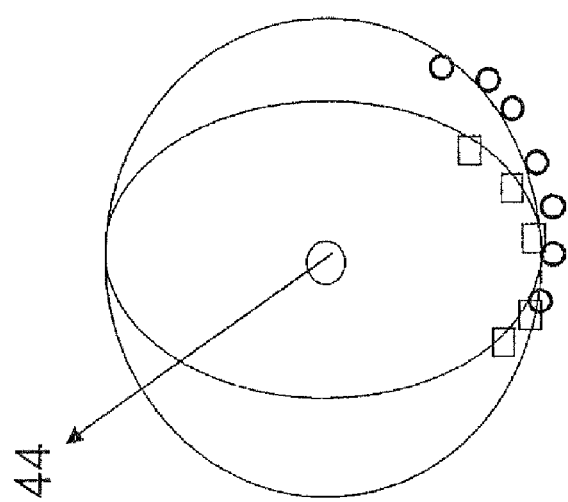

Referring to FIG. 5, when applied to hip procedures, the system is laid out as illustrated. In this example the central process unit 16 is a single computer on a cart 37, in conjunction with an optical tracking system 35 for real-time spatial localization of anatomy 1, 2 and specialized instruments 39. Input devices 36 are employed to allow users to interact with the system in a manner conducive to, for example, an operating room environment.

A cup 9 is placed in the joint and stem 12 is inserted into the cup 9. The cup 9 may be a trial cup used for determining placement of a final cup. As is known in the art, a trial cup may be better suited for determining placement prior to actual placement of a final cup. For example, if it is later determined that another size of cup would better suit the particular joint, then a more expensive cup is not wasted in the determination procedure. Devices 52 capable of being tracked by the spatial localizer 35 with high accuracy are then affixed rigidly to the pelvis 1 and femur 2. The exact placement and orientation of these devices will depend on the manner in which the overall joint replacement is being conducted and the placement of the spatial tracking device 35 in, for example, an operating room.

Figure 17:
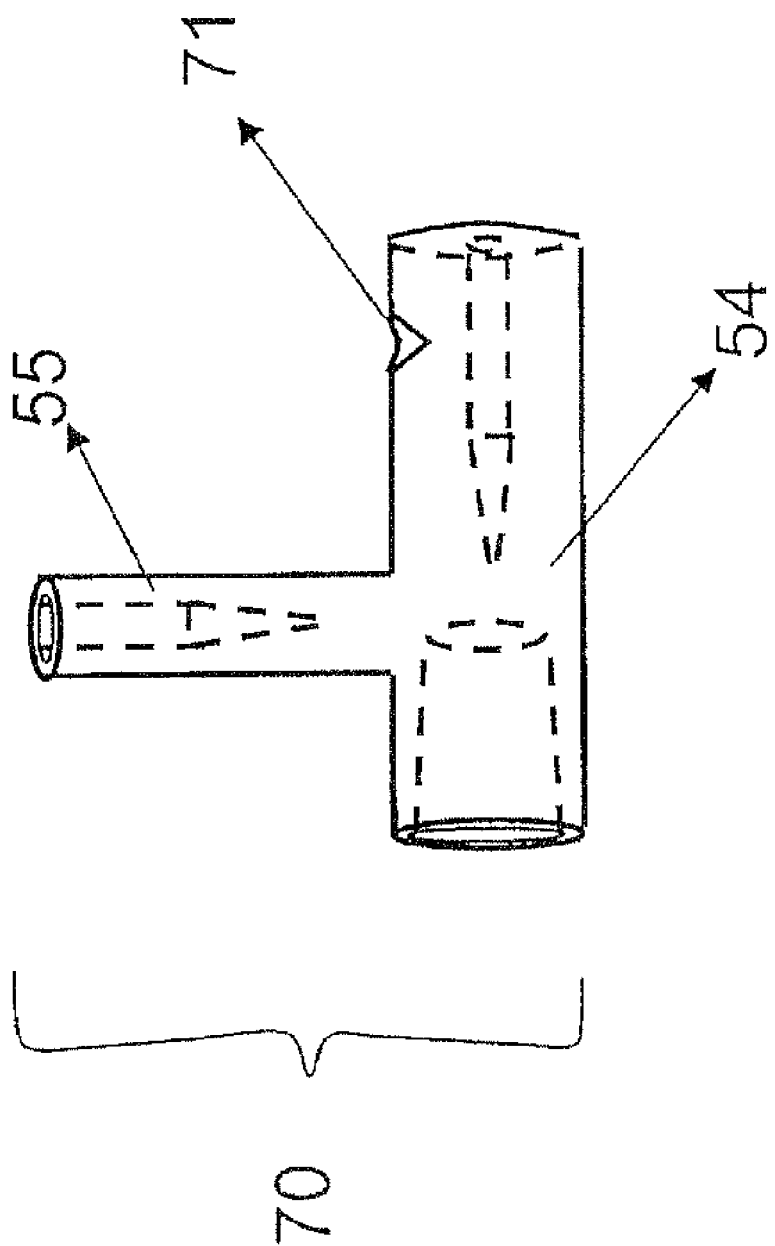
FIG. 17 illustrates example of prosthesis femoral stem calibration device.

Referring to FIG. 17, with the trackable devices 52 attached to the patient, the orientation and position of the stem component 12 can be determined, for example, by use of a calibration device 70 that provides for accurate placement of the calibration device relative to the femoral component neck 13 and for at least one fixed probe location for locating a spatially tracked probe 56 relative to the calibration device, such as for example calibration device 70 that facilitates determining the center of the prosthetic femoral head 11 and the axis of the prosthetic femoral neck 13. The probe location and direction is, or a series of probe locations and directions are, recorded relative to a reference 52 attached to the femur 2 by a registration module 64 for calculating the center of the femoral component head 11 and axis of the component neck 13.

The femoral calibration device 70 is made from rigid materials that can be sterilized, such as stainless steel. The device has a primary cylinder 54, a secondary cylinder 55 and a small divot 71 on the primary cylinder 54 such that the normal of the divot is parallel to a longitudinal axis of the secondary cylinder 55 and the position of the divot is outside the secondary cylinder.

Figure 18:
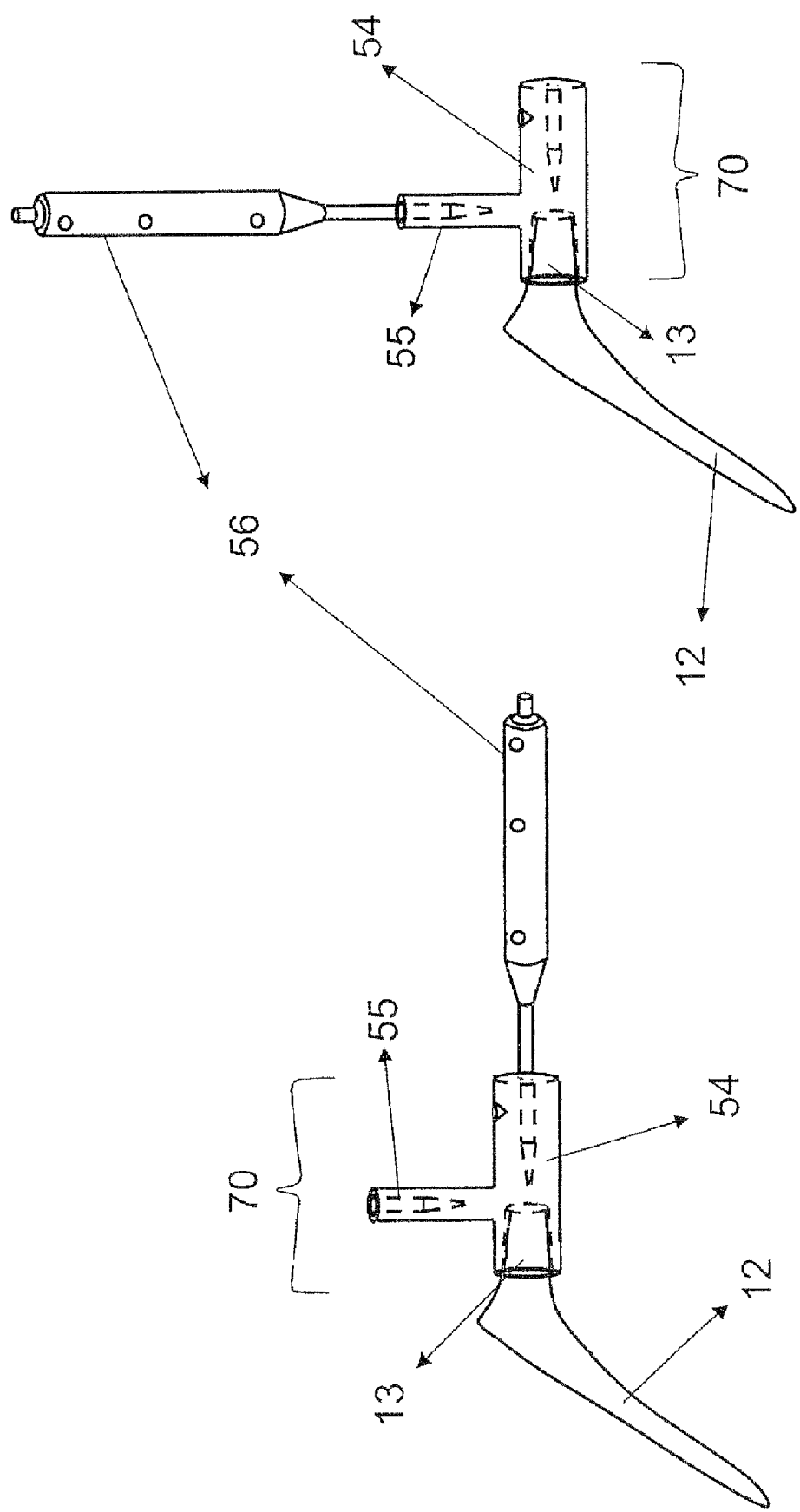
FIG. 18a illustrates an embodiment of a prosthetic femoral stem calibration device on a stem and with a probe in a first location.
FIG. 18b illustrates the embodiment of FIG. 18a with the probe in a second location.

Referring to FIG. 18a, one end of the primary cylinder 54 allows the device to be fitted to the exposed end of inserted femoral component. The other end of the primary cylinder 54 allows a spatially tracked probe 56 to be inserted into it. This other end of the primary cylinder 54 is an example of an alignment receptacle for a spatially tracked probe 56. When fitted onto the exposed end of the inserted femoral component 13 the calibration device 70 can be rotated about axis of the prosthetic femoral neck 13 without displacing from it. The secondary cylinder 55 also allows a spatially tracked probe 56 to be inserted into it. The secondary cylinder 55 is an example of an alignment receptacle for a spatially tracked probe 56. The divot 71 on the primary cylinder 54 allows a spatially tracked probe to be positively seated in it such that the probe 56 is aligned to the longitudinal axis of the secondary cylinder 55.

The device 70 allows the system to capture spatial information sufficient for determination of the center of the prosthetic femoral head 11 and the axis of the prosthetic femoral neck 13 using at least three different methods. A user employs one of the system input components to indicate the method being used. In each method, the calibration device 70 is fitted onto the exposed end of the inserted prosthetic femoral component 13. In a first method FIG. 18a, the user places a spatially tracked probe 56 into the free end of the primary cylinder and indicates to the system when the probe is positively seated in the calibration device 70. A registration module 64 captures the spatial localization information for the probe 56 and the trackable device 52 attached to the femur. The axis of the prosthetic femoral neck 13 is defined by the orientation of the probe 56 and the center of the femoral head 11 is derived from the location of the probe tip, which, when positively seated in the calibration device 70, has a known relationship with the center of the prosthetic femoral head 11.

Referring to FIG. 18b, in a second method the user places the probe 56 in the secondary cylinder 55 and indicates to the system to start collecting spatial localization information for calibration purposes. With the probe 56 firmly seated in the secondary cylinder 55 the user then rotates the calibration device back-and-forth about the axis of the prosthetic femoral neck 13.

The registration module 64 continues to collect spatial localization information for the probe 56 and the trackable device 52 attached to the femur 2 until it has enough data for calibration purposes. The registration module 64 uses the series of probe 56 orientations as inputs to a minimization algorithm, which will be understood by those skilled in the art. The results of the minimization are used to derive the center of the femoral head 11. A line parallel to the normal of the plane defined by the movement of the probe 56 and which passes through the derived center of the femoral head 11 is used to determine the axis of the prosthetic femoral neck 13. Using a third method for calibration, the user places a spatially tracked probe 56 into the secondary cylinder 55 and indicates to the system to capture spatial localization information for the probe 56 and the trackable device 52 attached to the femur 2. The user then moves the probe 56 to the divot 71 on the primary cylinder 54 and indicates to the system to again capture spatial localization information for the probe 56 and the trackable device 52 attached to the femur 2.

The registration module 64 uses the two locations of the probe 56 to define a line parallel to the axis of the prosthetic femoral neck 13. The axis of the prosthetic femoral neck 13 and center of the prosthetic femoral head 11 are then derived by the registration module 64 based on a known relationship between the calibration device 70 and the prosthetic femoral stem 12.

Regardless of the calibration method used, the system uses captured spatial localization information to determine and record the center of the prosthetic femoral head 11 and the axis of the prosthetic femoral neck 13.

As will be evident to those skilled in the art, other calibration devices allowing for capture of such localization information using only one or two of the above three methods could be constructed. Each such calibration device may be usable in more limited circumstances; however, they can also be useful. A set of calibration devices could be employed to allow for use in a variety of circumstances.

Referring to FIGS. 6-8 and 21, the user can define a functional coordinate system for the joint 42. The functional coordinate system 42 simply acts as a frame of reference for the display of visual data later and is defined by first moving the limb in abduction/adduction 40 to estimate the sagittal plane 80 and then flexion/extension 41 in order to estimate the frontal plane 81. The evaluation of these movements being done by the calculation of joint movements module 59.

The functional coordinate system module 60 captures spatial data on the movement of the limb by virtue of the trackable targets 52 attached to the anatomy. The data collected during the abduction/adduction and flexion/extension is also used to define a hip center of rotation 43. The functional coordinate system module 60 calculates the functional coordinate system 42. The hip center of rotation 43 is used for the origin and the axes are calculated with respect to the normals of the defined planes. The functional coordinate system is recorded relative to the pelvic reference.

Figure 15B:
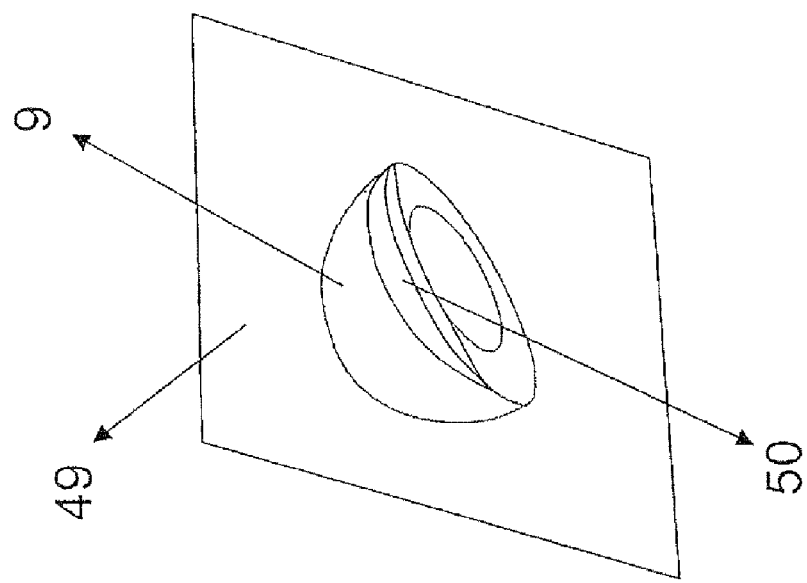
FIGS. 15a and 15b illustrate example anatomical evaluations of cup placement.
Figure 15A:
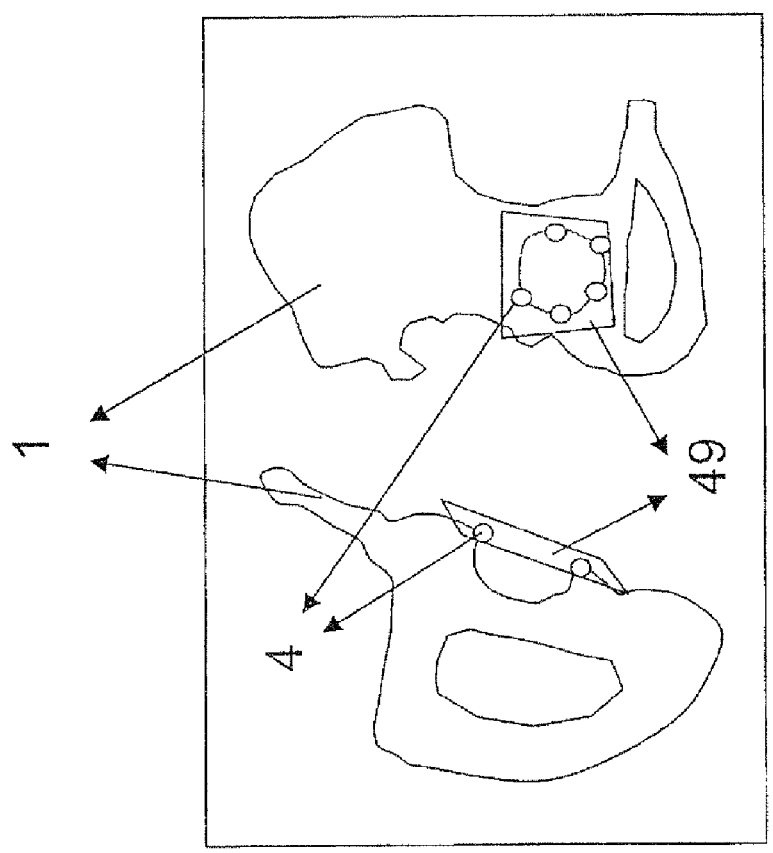
Figure 22:
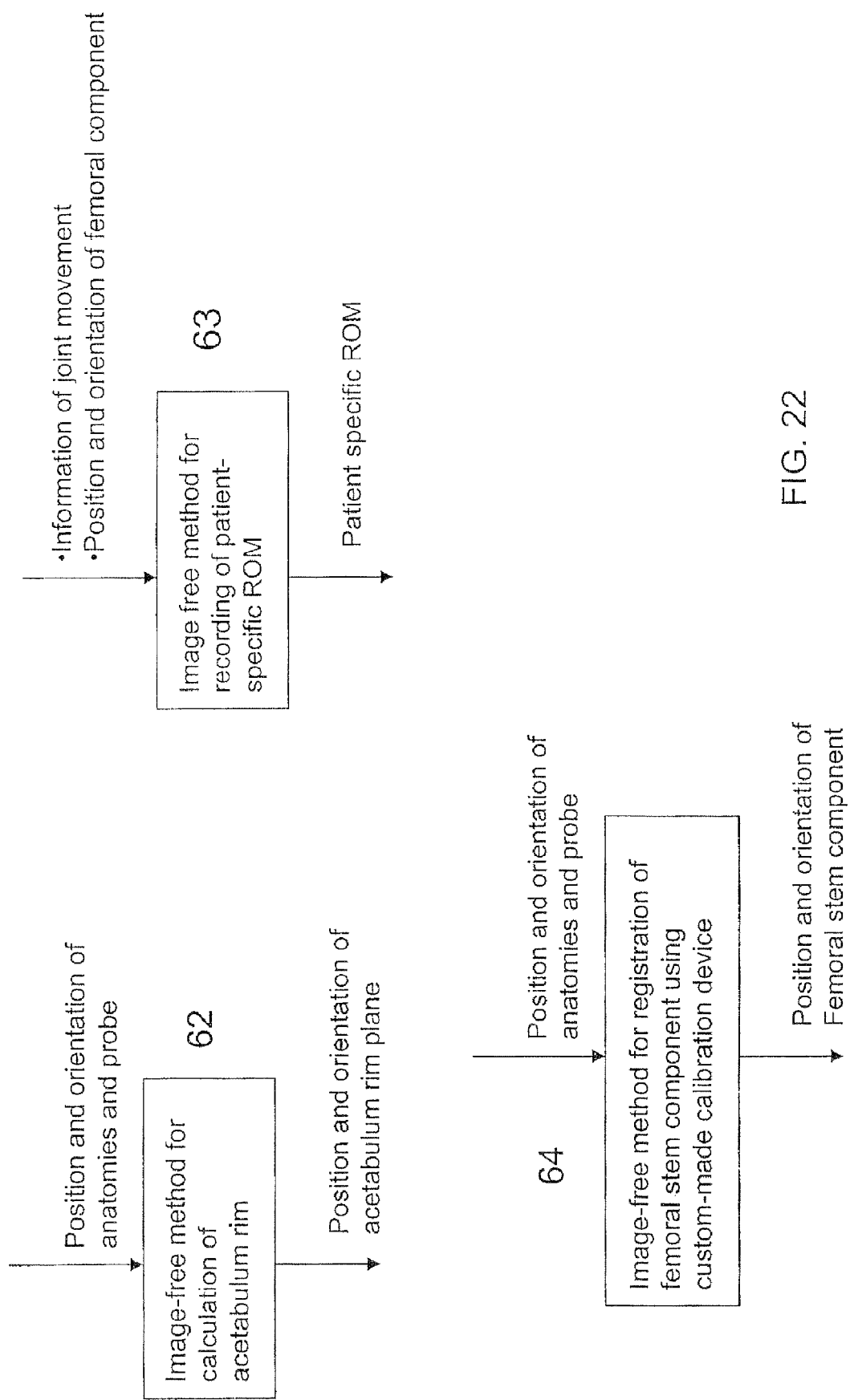
FIG. 22 identifies system modules and certain inputs and outputs for calculation of socket rim, registration of prosthetic stem and recording of patient range of motion.

Referring to FIGS. 15 and 22, information on the local anatomy can be obtained by palpation of the socket rim 4 with a spatially tracked probe 56. The socket rim module 62 records the palpations of the rim 4 and determines the plane of the rim 49 using 3 or more palpated points. Palpation of local anatomy does not suffer from the problems of accuracy and infection risk associated with palpation of global anatomy (such as that which would be required to define the pelvic plane). The locally palpated points are used to define a plane 49 that represents the boundary of bony coverage for an implanted prosthetic cup 9. The cup placement module 61 when optimizing cup placement uses it later.

Figure 9:
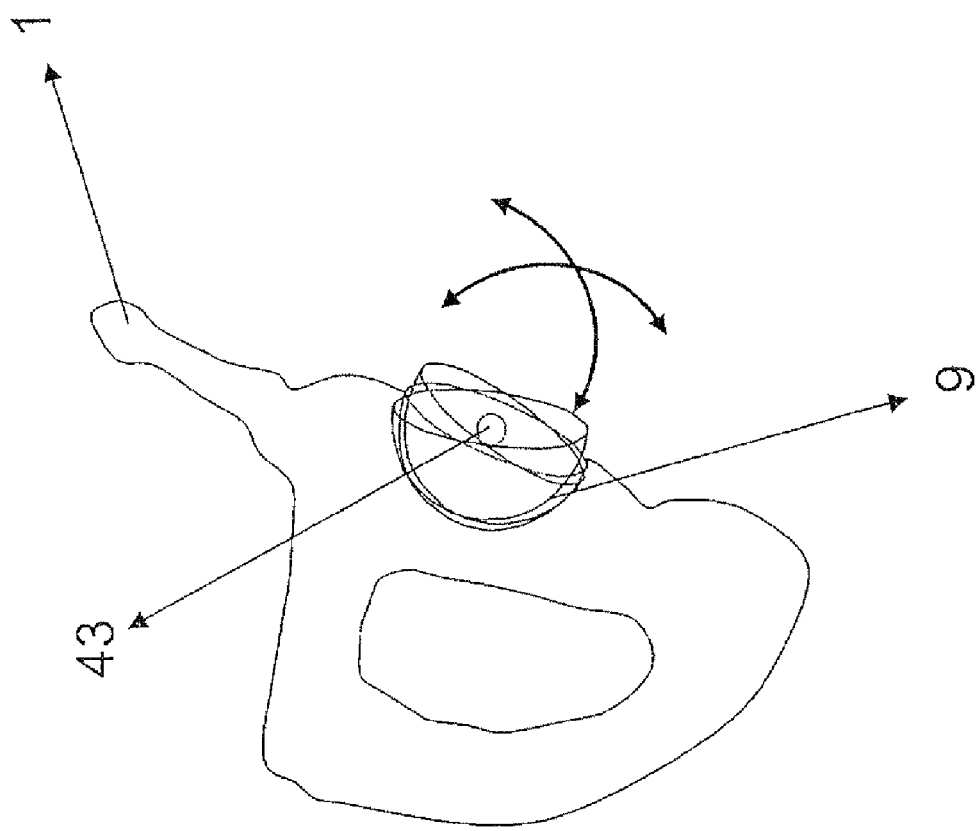
FIG. 9 shows freedom of a cup to rotate about the socket center of rotation.
Figure 10:
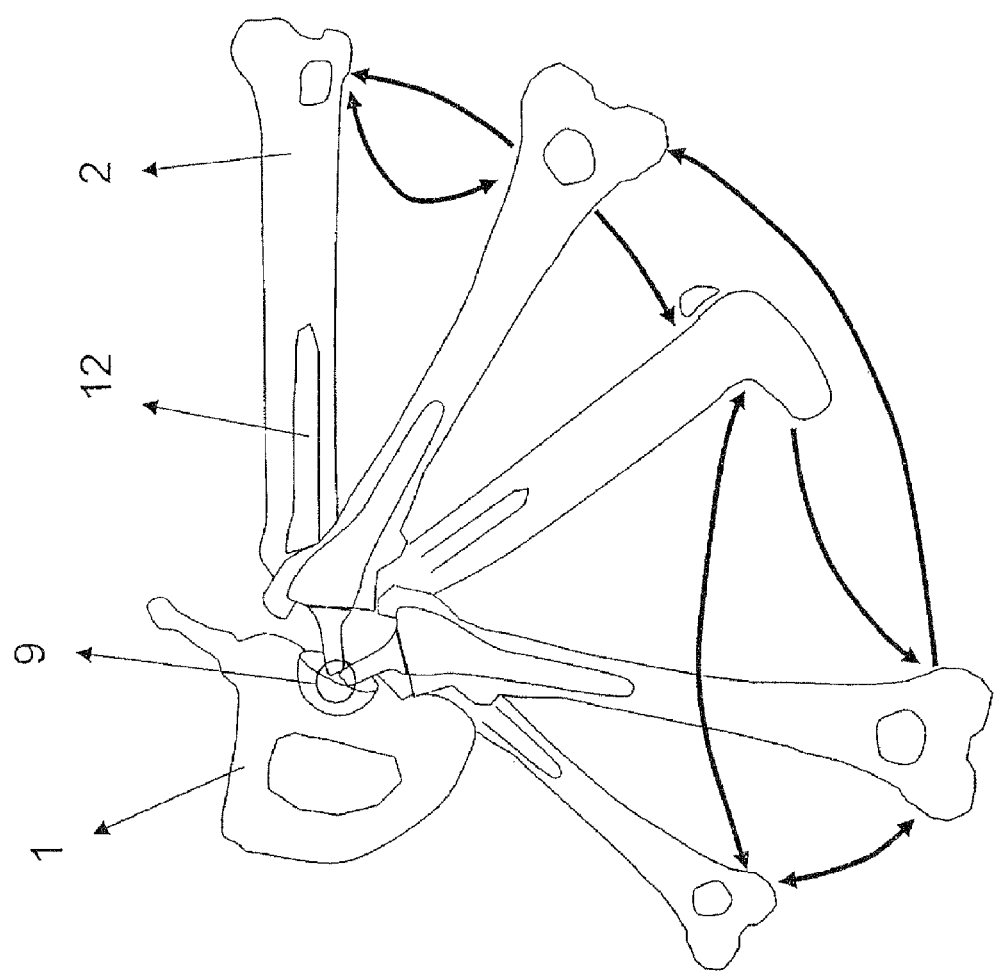
FIG. 10 demonstrates an example definition of a post-operative range of motion.
Figure 12B:
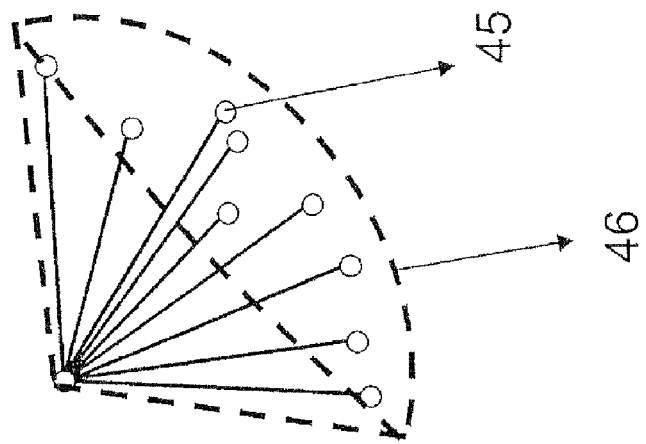
FIGS. 12a and 12b illustrate example methods for determining patient-specific impingement free range of motion for the method of FIG. 4.
Figure 12A:
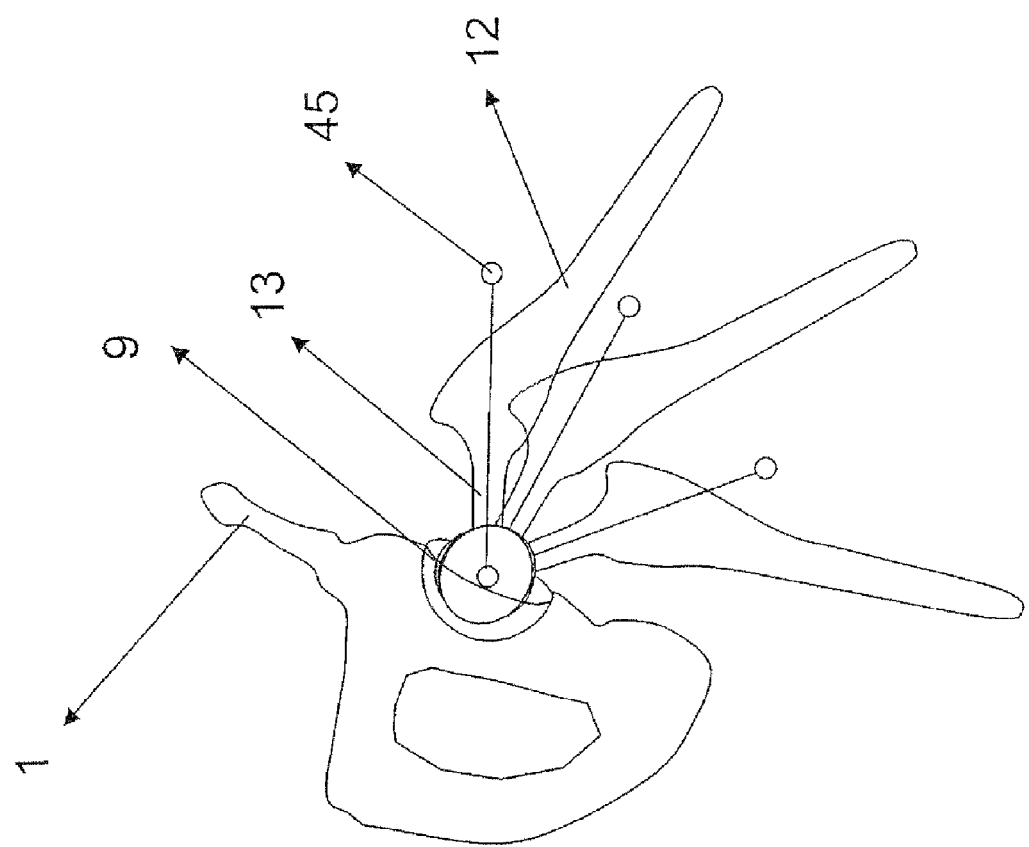

A patient specific ROM (range of motion) is then performed with the trial cup component 9. Referring to FIG. 9, as the cup 9 is not fixated, it can change orientation in the reamed socket 3 without altering its center of rotation 43. Referring to FIG. 10, when performing the ROM, the user will move the joint in a manner that is representative of the lifestyle and daily activities of the patient. The patient-specific ROM module 63 records these movements using the navigator technology 17, the trackable devices 52 attached to the anatomies 1, 2, and the previously recorded prosthetic stem registrations. Referring to FIG. 11, in the impingement free zone of the ROM, the center of the femoral head 11 coincides with the center of rotation 43. The patient-specific ROM module 63 determines impingement 44 to have occurred when movement between the center of the femoral head 11 and center of rotation 43 exceeds an acceptable tolerance. This type of movement will occur for the following types of impingement: bony-to-bony, bony-to-stem prosthesis, bony-to-soft tissue and soft tissue-to-soft tissue.

Figure 13B:
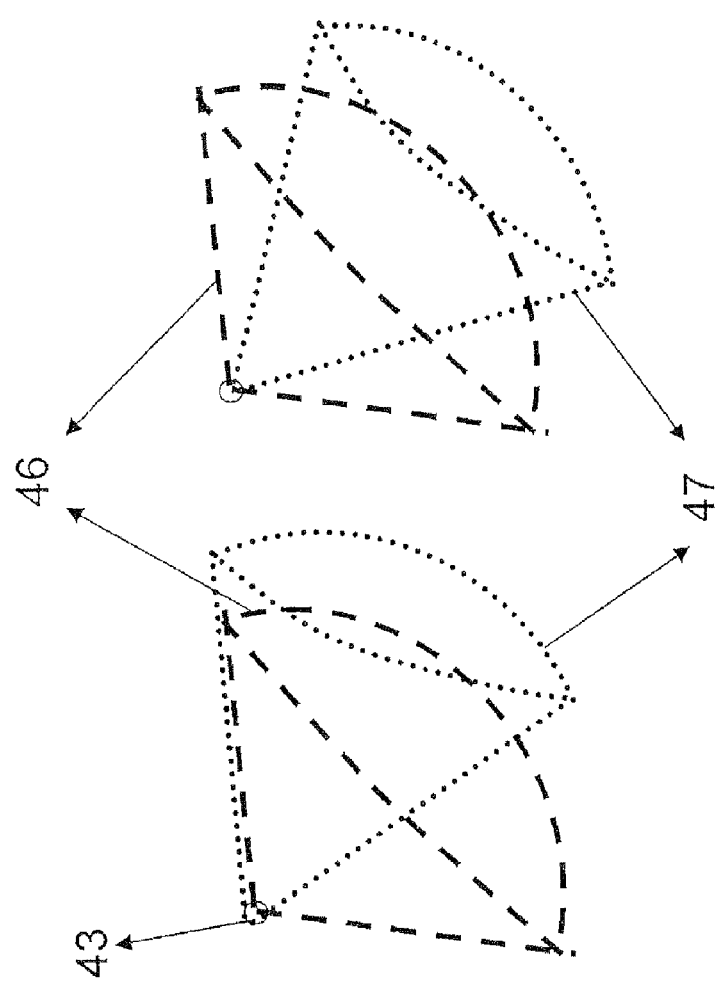
FIGS. 13a and 13b illustrate example methods for determining an impingement free zone for the prosthetic components of FIG. 2.
Figure 13A:
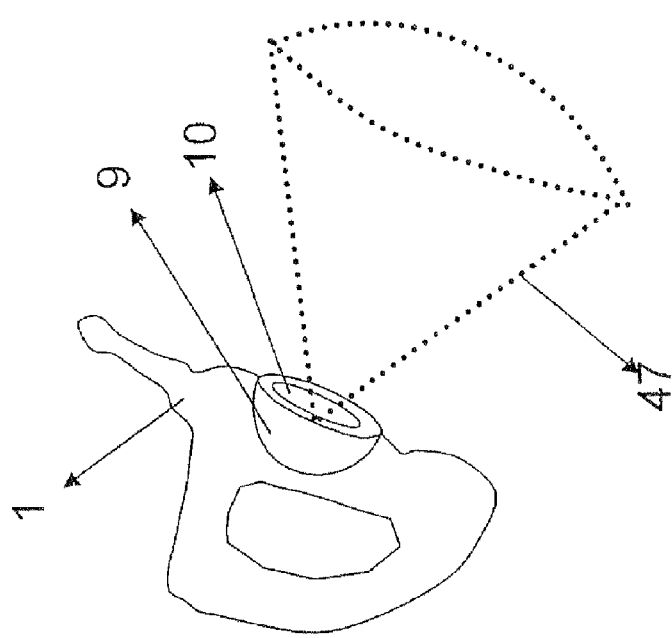
Figure 14B:
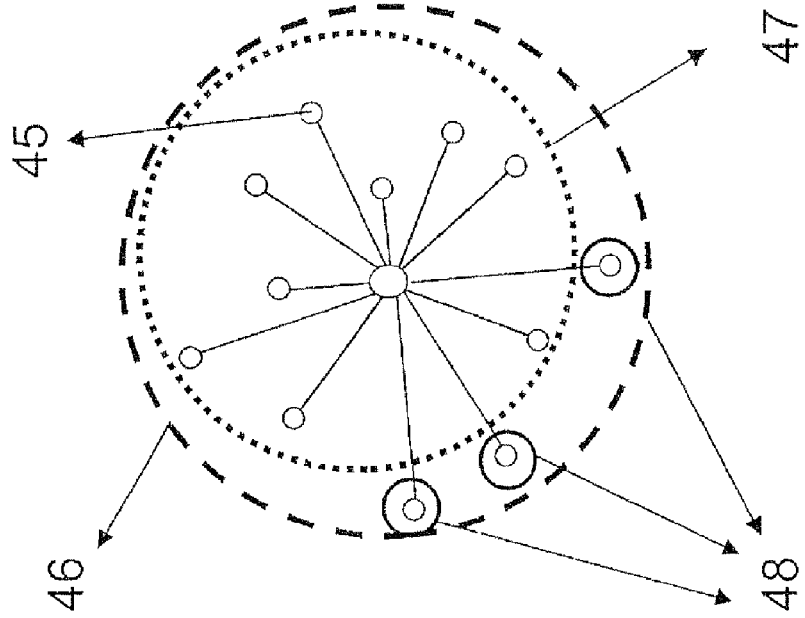
FIGS. 14a and 14b illustrate example kinematic evaluations of patient-specific ROM with respect to the prosthetic impingement-free ROM.
Figure 14A:
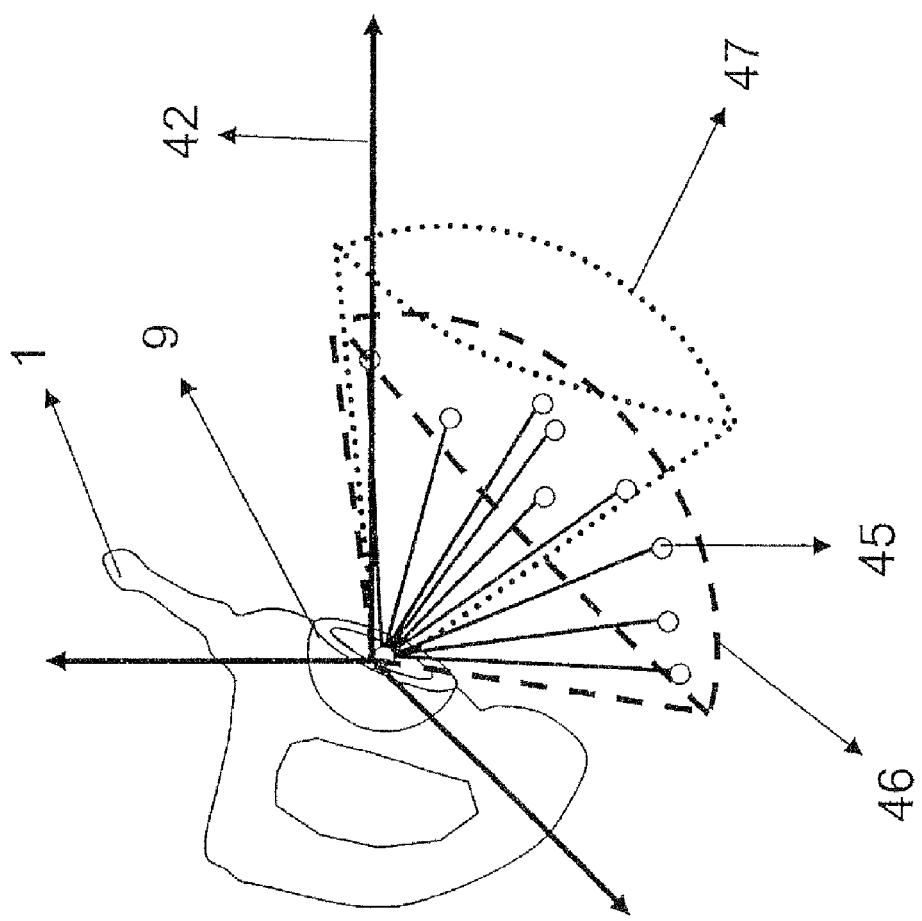
Figure 21:
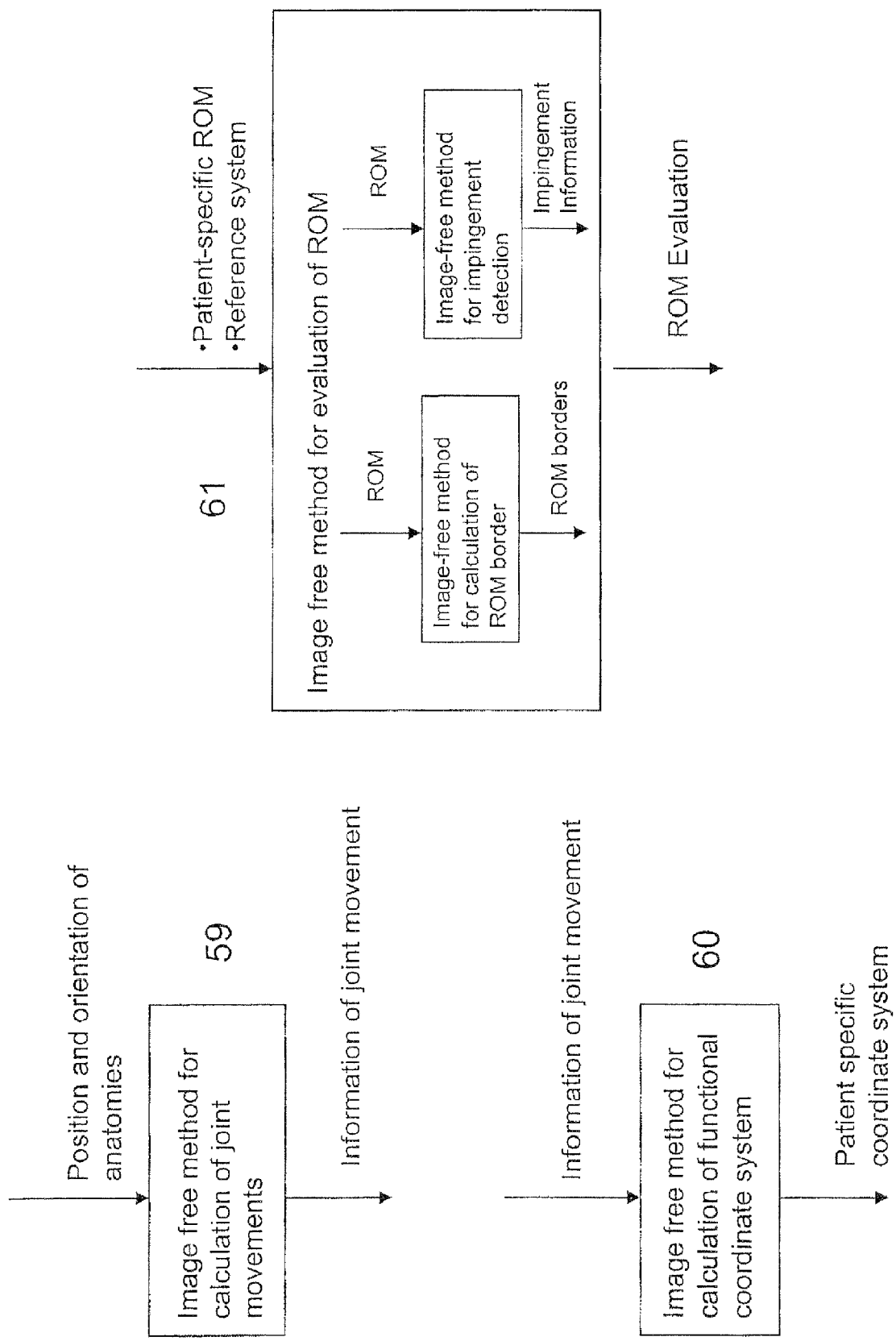
FIG. 21 identifies system modules and certain inputs and outputs for calculating joint movements, functional coordinates and range of motion evaluation.
Figure 23:
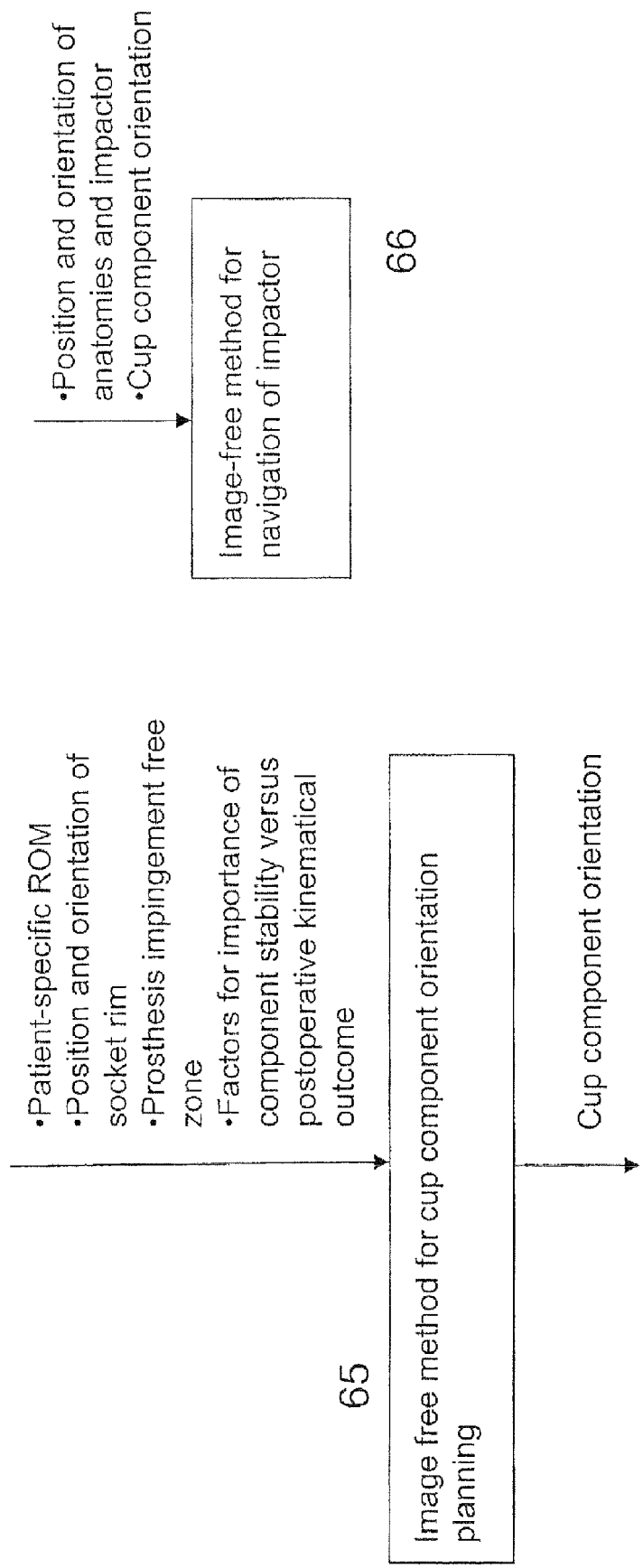
FIG. 23 identifies system modules and certain inputs and outputs for automatic planning of prosthetic cup placement and navigation of impactor to place prosthetic cup.

Impingement free orientations represent the patient specific ROM 46. Referring to FIGS. 13, 21 and 23, an impingement free zone 47 for the prosthetic cup 9 is calculated from geometric data of the implant system using the ROM evaluation module 61. The automatic planning module 65 determines an optimized orientation for the prosthetic cup 9. Referring to FIG. 14, the optimized orientation is determined firstly by aligning the impingement free zone 47 of the prosthetic cup 9 with respect to the patient-specific impingement free ROM 46. Referring to FIG. 15, the optimized orientation is further refined by maximizing bony coverage of the cup 9 within the socket 3 as determined, for example, by the amount of cup 9 within the socket rim 4 determined previously.

Graphical and numeric feedback is provided to the surgeon that illustrates the patient specific ROM 46 relative to the prosthetic cup impingement-free zone 47. Areas of overlap are impingement free and areas not overlapping indicate areas where impingement will occur post-operatively 48. Visual and numeric feedback is also provided to illustrate the bony coverage of the prosthetic cup 50.

A user may elect at this point to accept a planned prosthetic cup placement or to perform corrective actions to decrease impingement and/or increase bony coverage. Actions that a user may perform include, but are not limited to: osteophyte removal, soft-tissue release, prosthetic changes or adjustment the criteria for the optimization algorithm. In the preferred embodiment the system allows for the prediction of results of the correction. After the correction is performed, a user can validate it through repetition of earlier steps.

Figure 19:
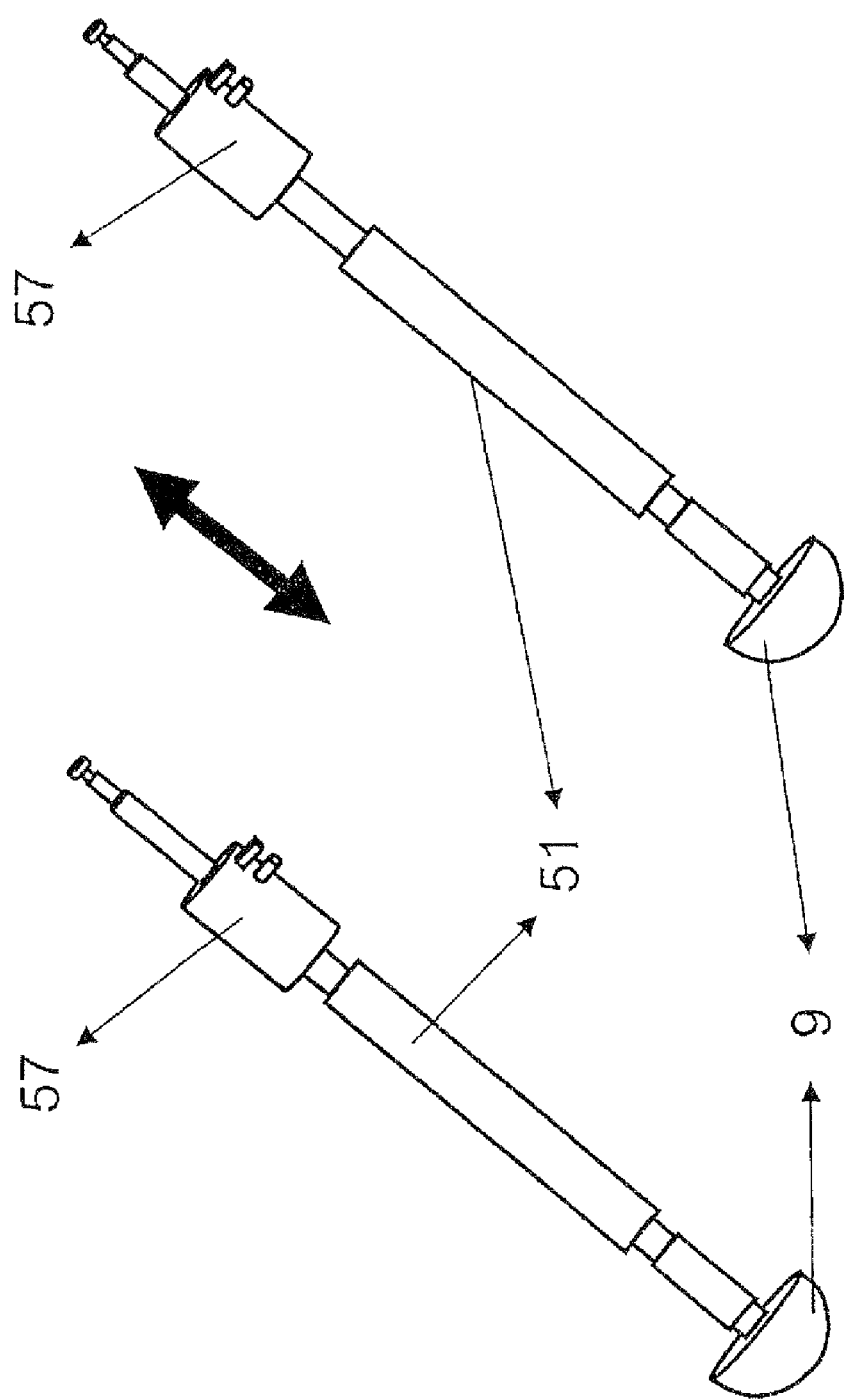
FIG. 19 illustrates an impactor and an embodiment of a shock-absorbing mount for a trackable device about the shaft of the impactor.
Figure 20:
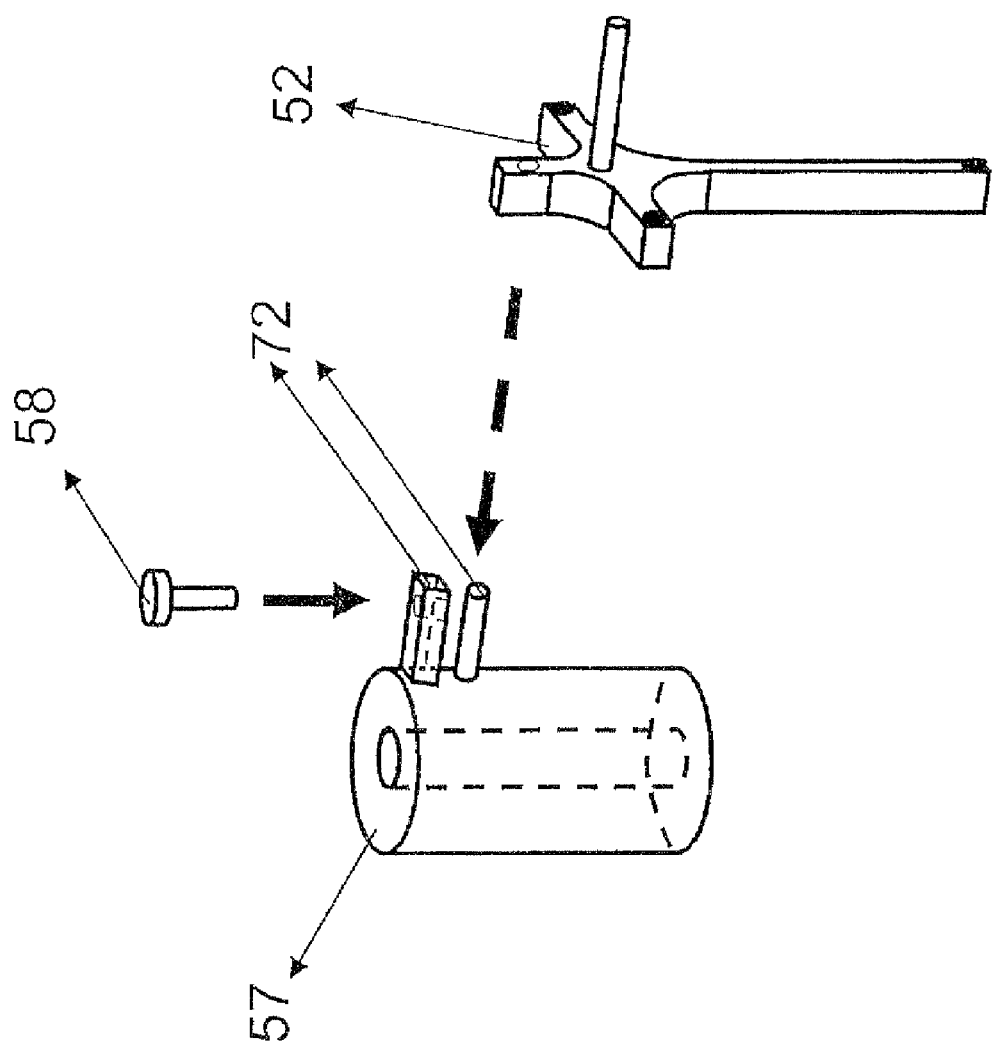
FIG. 20 illustrates stable fixation of trackable device to impactor mounting device.

Once a placement of the cup 9 is determined, an impactor 51 may be used to guide the cup 9. Referring to FIG. 19, a mount 57 that can have a trackable device 52 attached to it is placed over a shaft of a known impactor 51 such that the longitudinal axis of mount 57 and impactor align. The mount 57 is made of rigid materials that can be sterilized. Referring to FIGS. 20 and 23, the mount 57 has a cylinder for placement over a shaft of the impactor 51, pins 72 that allow the trackable device 52 to be attached to the mount 57 and a tightening mechanism 58 to hold the trackable device 52 rigidly to the mount. The mount 57 is free to rotate about the shaft of the impactor 51 as well as to move up and down along the shaft of the impactor. The mount 57 is rotated around the shaft to achieve an orientation of the trackable device 52 appropriate for spatial tracking given the type and positioning of the navigator components 17.

The navigation module 66 provides qualitative and quantitative feedback to the user to assist in the cup placement. The ability of the mount 57 to move along the shaft of the impactor 51 creates a shock absorption effect when the impactor is struck with a hammer, of the type commonly used for such purposes, to fixate the prosthetic cup 9 into the socket 3. This shock absorption effect reduces the likelihood that a trackable device 52 will loosen from the mount 57 or components of the trackable device 52 will loosen, such as, for example, retroreflective spheres which have been pressure fitted onto posts of the trackable device.

Figure 16B:
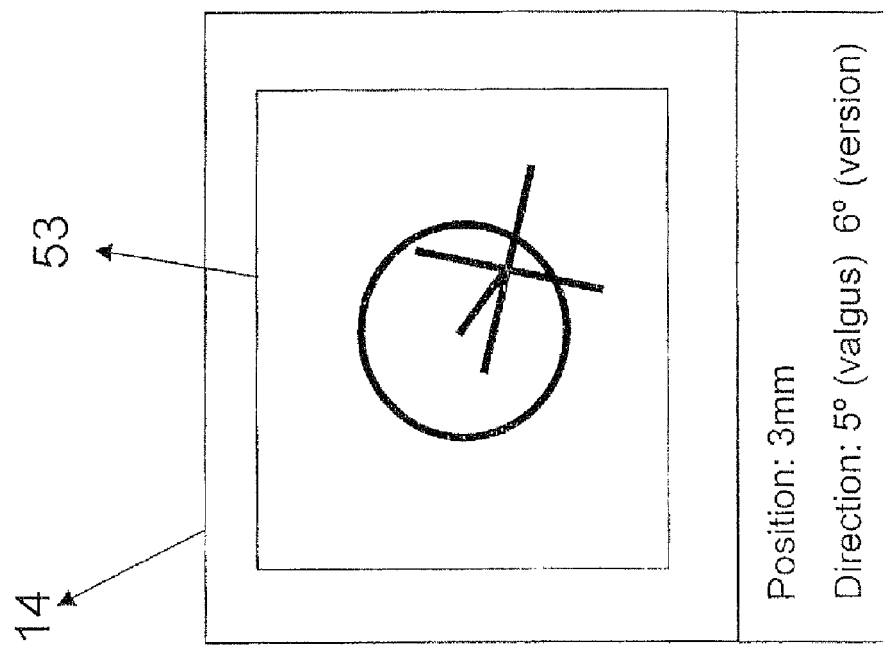
FIGS. 16a and 16b are illustrative of navigating a prosthesis to a planned placement using embodiments of aspect of the invention.
Figure 16A:
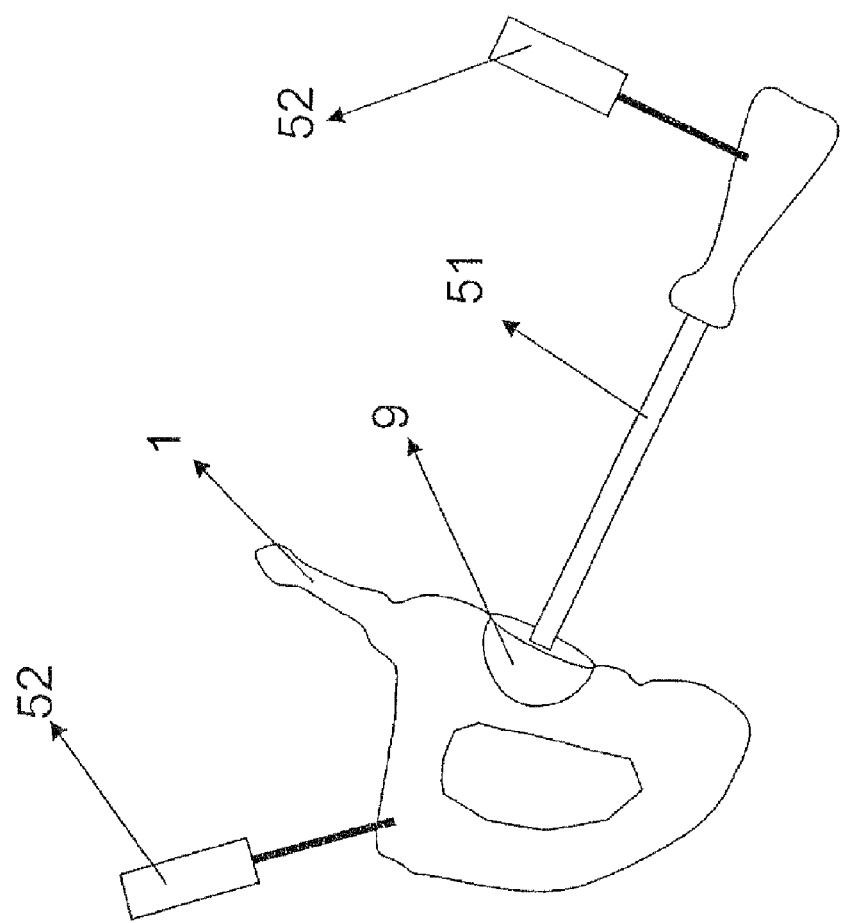

Referring to FIG. 16, graphical 53 and numeric feedback is provided by the system to assist in achieving the placement by the navigation module 66. A trackable device 52 may be otherwise rigidly held to the mount 57.

Referring again to FIG. 19, an impactor 51 with shock absorption is provided. It will be understood that use of the impactor 51 with shock absorption may be used generally for cup placement and is not limited to use in association with use with the system and other methods described herein.

The method in some embodiments provides a method for assisting a surgical intervention, such as a hip replacement, that does not require imaging and is based on the function of a joint, not just its bony anatomy. The method intrinsically accounts for effects of soft tissue, bony anatomy, prosthesis design, component placement and their interactions.

The method may be patient specific and not based only on standardized orientations for an implant. The method may use the function of a joint to indicate to a user where, and how, joint function is limited. In some embodiments this information allows a user to determine actions to take in order to correct the function. Such actions may include, but are not limited to, osteophyte removal, soft tissue release or altering implant selection.

Using patient-specific joint function to define the boundaries may avoid some limitations associated with using only bony landmarks or a simulated ROM including implicitly accounting for bony anatomy and soft tissue affects on the joint and avoiding time and costs associated with imaging and surface model reconstruction. Further, those bony landmarks that may be used in some embodiments of the method are generally relatively easy to palpate.

The functional data of the joint, combined with the known geometry and functional range of the implant system is used in some embodiments to determine a desired placement of the implant to improve the functional outcome and the stability of the implant. As the functional data is specific to the patient, it can be used to improve the placement for the patient's specific needs, lifestyle and activities.

Further, in some embodiments the user is able to parameterize the improvement in order to balance the needs for stability and range of motion considering the patient's lifestyle, activities and bone quality.

The method makes use of quantitative spatial information of patients' anatomy and instrumentation for the correction of the joint function. It will be understood by those skilled in the art that it is the data, not the mode of acquiring the data that is pertinent to the method.

Modes for acquisition of spatial data may include, but is not limited to, navigator technologies based on optics, mechanics, radio frequency, electromagnetism, acoustics, radiographic imaging, non-radiographic imaging, and so on.

It will be understood by those skilled in the art that various embodiments of the method will make use of different instrumentation for the placement of prosthetics. For example, an impactor has been described in the preferred embodiment for placement of a cup. However the principles of the invention do not exclude the use of any suitable instrumentation for the placement of a prosthetic component.

Those skilled in the art will understand that in some embodiments the method may use a functional range-of-motion and prosthesis geometry in the absence of a functional coordinate system to achieve a patient-specific functional placement of prosthesis.

It will be clear to those skilled in the art that the principles of the invention is applicable to joints in general including, but not limited to, hip, knee, shoulder, elbow, and so on. Further, it will be understood that the method and principles of the invention are applicable to forms of joint correction that do not involve implantation of prosthesis, such as patient-specific correction of joint function through osteophyte removal and/or soft tissue adjustments.

It will be clear to those skilled in the art that the principles of the invention is applicable to joints in general including, but not limited to, hip, knee, shoulder, elbow, and so on. Further, it will be understood that the method and principles of the invention are applicable to forms of joint correction that do not involve implantation of prosthesis, such as patient-specific correction of joint function through osteophyte removal and/or soft tissue adjustments.

By way of example an embodiment of the method using a computer monitor for an output device has been described. Other embodiments of the method may use other forms of output, including, but not limited to, tactile devices and audio devices.

It will be understood by those skilled in the art that this description is made with reference to the preferred embodiments and that it is possible to make other embodiments employing the principles of the invention which fall within its spirit and scope as defined by the following claims.

What is claimed is:

1. A method of determining desired placement of a cup within an anatomical joint having a socket and having a stem with a center of rotation, the cup having a given range of motion for the stem, the method comprising:
    placing the cup in the socket such that movement of a center of rotation of the cup is limited, while rotation of the cup about the center of rotation is permitted;
    reducing the stem and cup such that the center of rotation of the stem and the center of rotation of the cup are concentric;
    determining a range of motion of the joint by moving the stem, and
    aligning the range of motion of the cup and the determined range of motion of the joint.

2. The method of claim 1 further comprising palpating a rim of the socket in order to determine a plane of the rim, and, at the same time as aligning the range of motion of the cup and the determined range of motion of the joint, aligning the cup within the socket to provide desired bony coverage to the cup within the rim.

3. The method of claim 1 further comprising modifying the range of motion of the joint to improve the alignment of the range of motion of the cup and the range of motion of the socket.

4. The method of claim 3 further compromising repeating the steps of claim 1.

5. The method of claim 2 further compromising modifying the joint to change spatial placement of the cup within the socket to improve bony coverage to the cup within the rim.

6. The method of claim 5 further comprising repeating the steps of claim claim 2.

* * * * *

UNITED STATES PATENT AND TRADEMARK OFFICE
CERTIFICATE OF CORRECTION

| | | |
|---|---|---|
| PATENT NO. | : 8,177,850 B2 | Page 1 of 1 |
| APPLICATION NO. | : 12/339791 | |
| DATED | : May 15, 2012 | |
| INVENTOR(S) | : John Rudan, Randy E. Ellis and Manuela Kunz | |

It is certified that error appears in the above-identified patent and that said Letters Patent is hereby corrected as shown below:

Column 12, claim 6, line 57 delete the duplicate word "claim".

Signed and Sealed this
Tenth Day of July, 2012

David J. Kappos
*Director of the United States Patent and Trademark Office*